(12) United States Patent
Berglund et al.

(10) Patent No.: US 8,436,049 B2
(45) Date of Patent: May 7, 2013

(54) USES OF PENTAMIDINE AND RELATED COMPOUNDS

(75) Inventors: John Andrew Berglund, Eugene, OR (US); M. Bryan Warf, Eugene, OR (US); Catherine Matthys, Eugene, OR (US); Michael M. Haley, Eugene, OR (US); Cameron L. Hilton, Eugene, OR (US)

(73) Assignee: State of Oregon Acting By and Through the State Board of Higher Education on behalf of the University of Oregon, Eugene, OR (US)

( * ) Notice: Subject to any disclaimer, the term of this patent is extended or adjusted under 35 U.S.C. 154(b) by 334 days.

(21) Appl. No.: 12/918,696

(22) PCT Filed: Feb. 20, 2009

(86) PCT No.: PCT/US2009/034745
§ 371 (c)(1),
(2), (4) Date: Aug. 20, 2010

(87) PCT Pub. No.: WO2009/105691
PCT Pub. Date: Aug. 27, 2009

(65) Prior Publication Data
US 2010/0323993 A1    Dec. 23, 2010

Related U.S. Application Data

(60) Provisional application No. 61/030,494, filed on Feb. 21, 2008.

(51) Int. Cl.
*A01N 37/52*  (2006.01)
*A61K 31/155*  (2006.01)

(52) U.S. Cl.
USPC .......................................... 514/631; 514/637

(58) Field of Classification Search .................... 514/631
See application file for complete search history.

(56) References Cited

PUBLICATIONS

Antony et al., "Novel high-throughput eletrochemiluminescent assay for identification of human tyrosyl-DNA phosphodiesterase (Tdp1) inhibitors and characterization of furamidine (NSC 305831) as an inhibitor of Tdp1," *Nucleic Acids Research*, vol. 35, No. 13, pp. 4474-4484, 2007.
Bailly et al., "Sequence-selective binding to DNA of bis(amidinophenoxy)alkanes related to propamidine and pentamidine," *Biochem. J.*, vol. 323, pp. 23-31, 1997.
Chaires et al., "Structural Selectivity of Aromatic Diamidines," *J. Med. Chem.*, vol. 47, pp. 5729-5742, 2004.
Hao et al., "*Muscleblind-like 2 (Mbnl2)*—Deficient Mice as a Model for Myotonic Dystrophy," *Developmental Dynamics*, vol. 237, pp. 403-410, 2008.
Kino et al., "Direct Evidence that EXP/muscleblind Interacts with CCUG Tetranucleotide Repeats," *Basic Appl. Myol.*, vol. 13, No. 6, pp. 293-298, 2003.
Margolis et al., "DM2 intronic expansions: evidence for CCUG accumulation without flanking sequence or effects on *ZNF9* mRNA processing or protein expression," *Human Molecular Genetics*, vol. 15, No. 11, pp. 1808-1815, 2006.
Bodner et al., "Therapeutic Agents for Myotonic Dystrophy: Defining the Pharmacophore of Pentamidine," poster presented at 8th International Myotonic Dystrophy Consortium meeting, Nov. 30-Dec. 3, 2011 (1 page).

*Primary Examiner* — Sreeni Padmanabhan
*Assistant Examiner* — Layla Soroush
(74) *Attorney, Agent, or Firm* — Klarquist Sparkman, LLP

(57) ABSTRACT

Methods are provided herein for treatment of myotonic dystrophy and other toxic RNA diseases in a subject. In some examples, the method comprises administration of a compound that binds a nucleotide repeat expansion in a ribonucleic acid molecule, thereby treating the disease. In additional examples, the method comprises administration of a compound that disrupts binding of muscleblind-like proteins to an RNA nucleotide repeat expansion. Compounds for use in the disclosed method include pentamidine or heptamidine or derivatives thereof. Representative compounds are described herein.

13 Claims, 9 Drawing Sheets

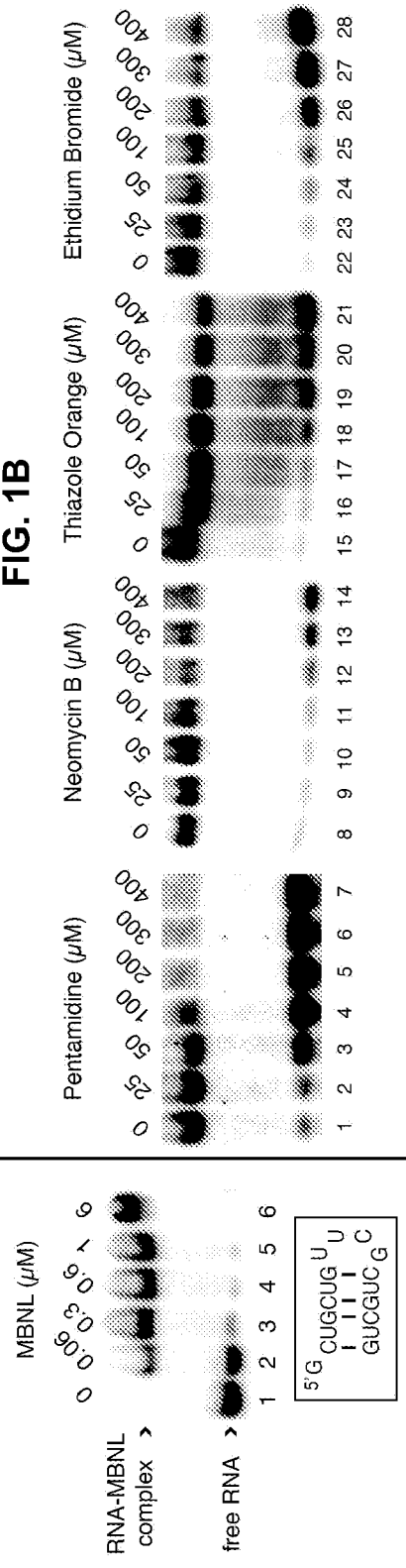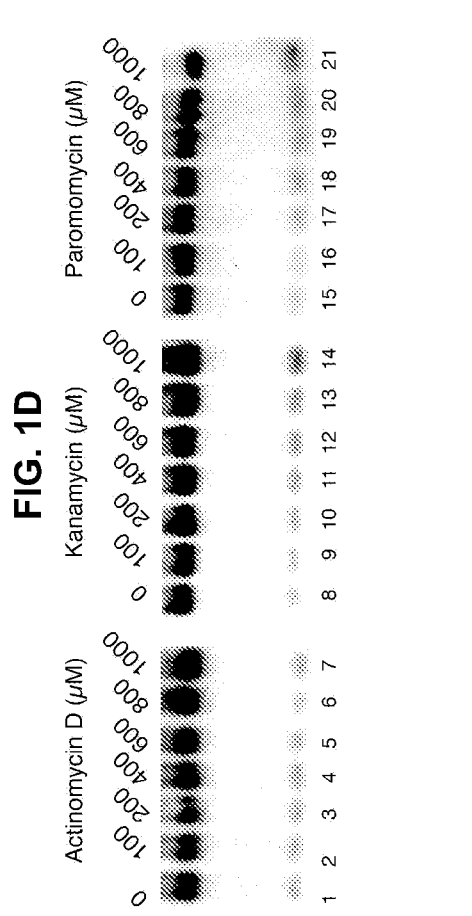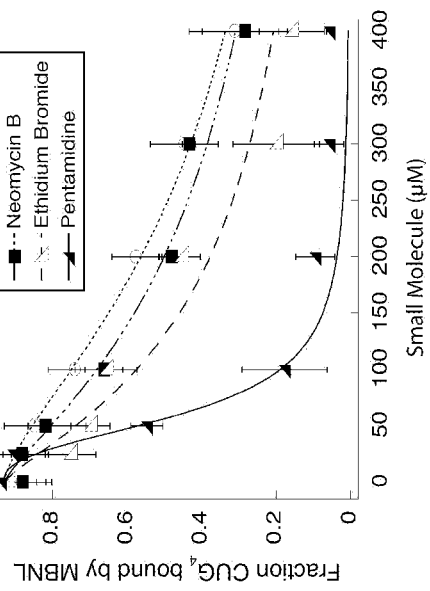

Pentamidine cTNT 32mer

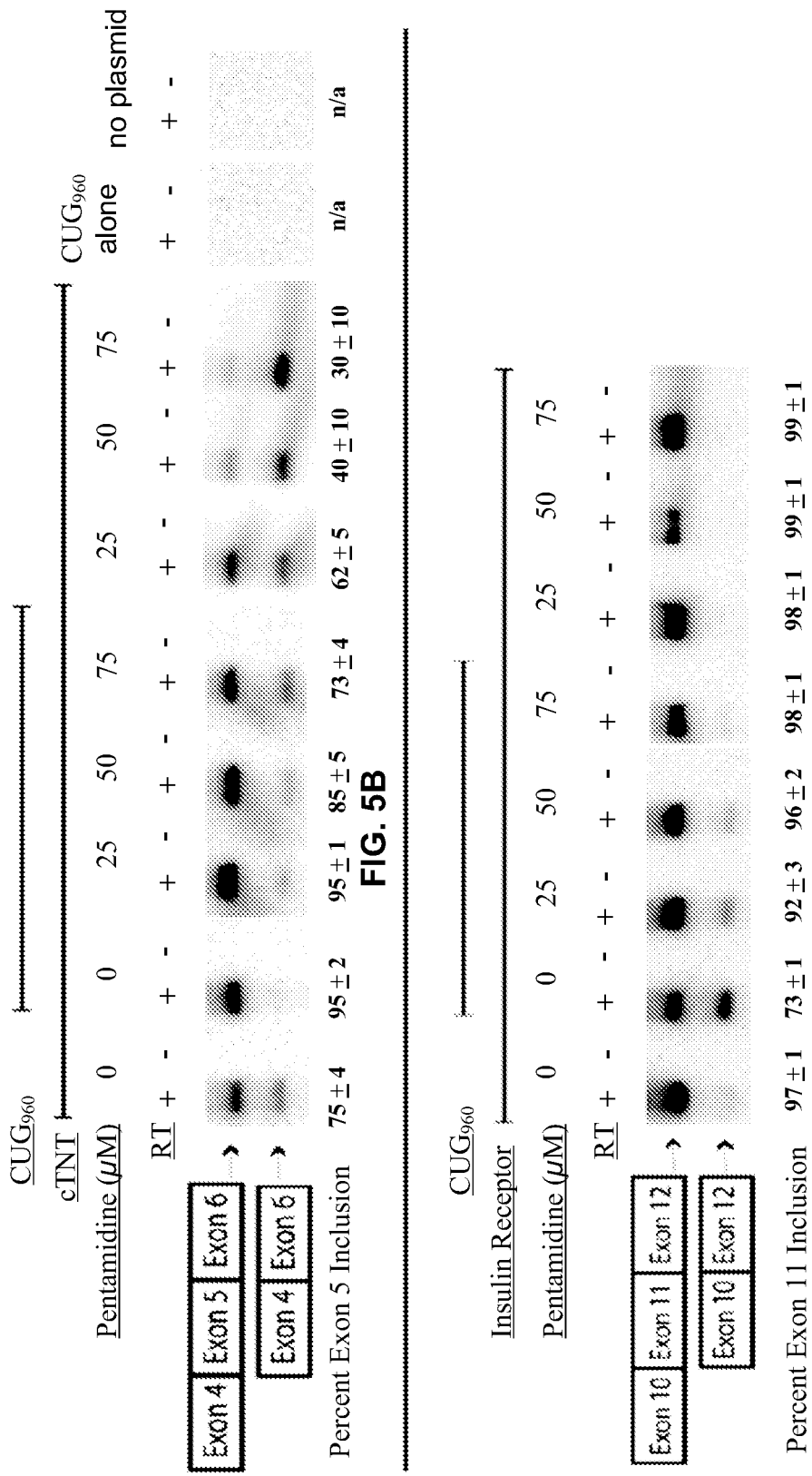

```
                              SEQUENCE LISTING

<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Cardiac troponin T forward oligonucleotide
      primer

<400> SEQUENCE: 1
gttcacaacc atctaaagca agatg                                           25

<210> SEQ ID NO 2
<211> LENGTH: 19
<212> TYPE: DNA
<213> ORGANISM: Artificial Sequence
<220> FEATURE:
<223> OTHER INFORMATION: Cardiac troponin T reverse oligonucleotide
      primer

<400> SEQUENCE: 2
gttgcatggc tggtgcagg                                                  19

<210> SEQ ID NO 3
<211> LENGTH: 34
<212> TYPE: DNA
<213> ORGANISM: Artificial Sequence
<220> FEATURE:
<223> OTHER INFORMATION: Insulin receptor forward oligonucleotide primer

<400> SEQUENCE: 3
gtacaagctt gaatgctgct cctgtccaag acag                                 34

<210> SEQ ID NO 4
<211> LENGTH: 25
<212> TYPE: DNA
<213> ORGANISM: Artificial Sequence
<220> FEATURE:
<223> OTHER INFORMATION: Insulin receptor reverse oligonucleotide primer

<400> SEQUENCE: 4
gccctcgagc gtgggcacgc tggtc                                           25

<210> SEQ ID NO 5
<211> LENGTH: 30
<212> TYPE: DNA
<213> ORGANISM: Artificial Sequence
<220> FEATURE:
<223> OTHER INFORMATION: PLEKHH2 forward oligonucleotide primer

<400> SEQUENCE: 5
cggggtacca aatgctgcag ttgactctcc                                      30

<210> SEQ ID NO 6
<211> LENGTH: 29
<212> TYPE: DNA
<213> ORGANISM: Artificial Sequence
```

```
<220> FEATURE:
<223> OTHER INFORMATION: PLEKHH2 reverse oligonucleotide primer

<400> SEQUENCE: 6
ccgctcgagc cattcatgaa gtgcacagg                                         29

<210> SEQ ID NO 7
<211> LENGTH: 24
<212> TYPE: DNA
<213> ORGANISM: Artificial Sequence
<220> FEATURE:
<223> OTHER INFORMATION: Chloride channel 1 forward oligonucleotide
      primer

<400> SEQUENCE: 7
tgaaggaata cctcacactc aagg                                              24

<210> SEQ ID NO 8
<211> LENGTH: 20
<212> TYPE: DNA
<213> ORGANISM: Artificial Sequence
<220> FEATURE:
<223> OTHER INFORMATION: Chloride channel 1 reverse oligonucleotide
      primer

<400> SEQUENCE: 8
cacggaacac aaaggcactg                                                   20

<210> SEQ ID NO 9
<211> LENGTH: 23
<212> TYPE: DNA
<213> ORGANISM: Artificial Sequence
<220> FEATURE:
<223> OTHER INFORMATION: Sarcoplasmic reticulum/endoplasmic reticulum
      calcium ATPase forward oligonucleotide primer

<400> SEQUENCE: 9
gctcatggtc ctcaagatct cac                                               23

<210> SEQ ID NO 10
<211> LENGTH: 20
<212> TYPE: DNA
<213> ORGANISM: Artificial Sequence
<220> FEATURE:
<223> OTHER INFORMATION: Sarcoplasmic reticulum/endoplasmic reticulum
      calcium ATPase reverse oligonucleotide primer

<400> SEQUENCE: 10
gggtcagtgc ctcagctttg                                                   20
```

USES OF PENTAMIDINE AND RELATED COMPOUNDS

CROSS REFERENCE TO RELATED APPLICATIONS

This is the §371 U.S. National Stage of International Application No. PCT/US2009/034745, filed Feb. 20, 2009, which was published in English under PCT Article 21(2), which in turn claims the benefit of U.S. Provisional Application No. 61/030,494, filed Feb. 21, 2008, which is incorporated by reference herein in its entirety.

ACKNOWLEDGMENT OF GOVERNMENT SUPPORT

This invention was made with United States government support pursuant to grant AR053903 from the National Institutes of Health; the United States government has certain rights in the invention.

FIELD

This application relates to methods for treatment of myotonic dystrophy or other toxic RNA diseases, in particular methods using small molecules, such as pentamidine and related compounds.

BACKGROUND

Myotonic dystrophy (DM) is one of many diseases under the umbrella of muscular dystrophy. DM is the most common form of adult onset muscular dystrophy, affecting 1 in 8000 people (Ranum & Day, *Am. J. Hum. Genet.* 74:793-804, 2004). DM is caused by an expansion of three or four nucleotide repeats: a CUG expansion in subjects with myotonic dystrophy type I (DM1), and a CCUG expansion in subjects with myotonic dystrophy type 2 (DM2). DM1 is responsible for the majority of subjects with myotonic dystrophy, while DM2 is relatively rare. In DM1, CUG repeats are found in the dystrophia myotonica-protein kinase (DMPK) gene on chromosome 19 (Aslanidis et al., *Nature* 355:548-551, 1992; Brook et al., *Cell* 68:799-808, 1992). In DM2, the CCUG repeats are found in the zinc finger 9 (ZNF9) gene, a gene on chromosome 3 encoding a zinc finger protein (Liguori et al., *Science* 293:864-867, 2001). For both DM1 and DM2 the repeats are found in non-translated regions of the pre-mRNA. In DM1 the expanded CUG triplet repeats are in the 3' untranslated region (UTR), unless alternative splicing occurs within this region of the DMPK transcript, in which case, the CUG repeats are within the last intron before the last exon (Tiscornia & Mahadevan, *Mol. Cell.* 5:959-967, 2000). The CCUG repeats in ZNF9 are within the first intron (Liguori et al., 2001).

Both DM1 and DM2 subjects display many of the same symptoms (myotonia, progressive muscle weakness and wasting, cataracts, and cardiac and developmental defects), strongly suggesting that both DM1 and DM2 work through the same or very similar mechanisms (Tapscott & Thornton, *Science* 293:816-817, 2001). The current model is that an RNA gain-of-function mechanism is responsible for causing DM, meaning that expansion of the CUG or CCUG repeats results in an RNA molecule that has a new function, apparently overriding other cellular pathways.

In the case of DM1, the normal length of the CUG triplet repeats in DMPK is in the range of 5-37 repeats, the "pre-mutation" range of repeats is 50-180, and the disease causing range is from 200 to greater than 2000 repeats (Ranum & Day, 2004). In the case of DM2, normal alleles have 11-26 CCUG tetranucleotide repeats, while pathogenic alleles have from 75 to more than 11,000 repeats. For DMPK, biochemical studies have shown that with just 11 CUG repeats, a stable triplet repeat stem-loop structure is able to form, and as the number of repeats increases so does the length and stability of the stem-loop (Napierala & Krzyzosiak, *J. Biol. Chem.* 272:31079-31085, 1997). The number of repeats and possibly the length of the stem correlate with the severity of DM; the larger the number of repeats, the more severe the symptoms of DM displayed by the subject (Ranum & Day, 2004).

SUMMARY

No treatment currently exists for either form of DM. Management is generally limited to treatment of the clinical manifestations of the disease, such as assistive devices, pain management, removal of cataracts, and cardiac monitoring. Thus, there is a need for treatments for DM.

This disclosure provides methods of treating disease caused by toxic RNA in a subject, comprising administering a compound that binds a nucleotide repeat expansion in an RNA molecule. Also provided are methods of treating myotonic dystrophy in a subject, comprising administering to the subject a compound that binds a nucleotide repeat expansion in an RNA molecule.

In some examples, a method of treating myotonic dystrophy is provided comprising administering a compound that binds an RNA trinucleotide repeat expansion, such as a CUG expansion. In a particular example, the nucleotide repeat expansion is a trinucleotide repeat expansion in the DMPK gene. In additional examples, the method comprises administration of a compound that binds an RNA tetranucleotide repeat, such as a CCUG repeat expansion. In a particular example the tetranucleotide repeat expansion is in the ZNF9 gene.

Also disclosed are methods of treating myotonic dystrophy using compounds that disrupt protein binding to nucleotide repeat expansions. In particular examples, the disclosed compounds disrupt binding of muscleblind-like proteins to CUG repeats of DMPK RNA or to CCUG repeats of ZNF9 RNA.

This disclosure provides compounds that may be used in methods of treating myotonic dystrophy or other toxic RNA diseases. In some examples, the compound is a small organic molecule, such as a diamidine, for example a compound having the structure:

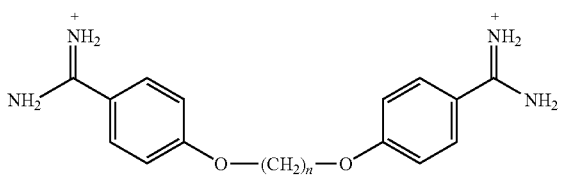

(1)

In other examples, the compound is a derivative of a diamidine. In particular examples, the compound is pentamidine or heptamidine, or a derivative thereof.

Methods of treating diseases caused by toxic RNA comprising administering to a subject a compound that binds an RNA nucleotide repeat expansion are disclosed herein. In particular examples, toxic RNA diseases include myotonic dystrophy types I and II, spinocerebellar ataxia type 8

(SCA8), fragile X tremor ataxia syndrome (FXTAS), and Huntington disease-like 2 (HDL2).

The foregoing and other objects, features, and advantages will become more apparent from the following detailed description, which proceeds with reference to the accompanying figures.

BRIEF DESCRIPTION OF THE DRAWINGS

FIG. 1A is a photograph of a gel-shift assay showing binding of MBNL to radiolabeled short CUG repeat RNA. The inset shows the short CUG repeat structure.

FIG. 1B is a photograph of a gel-shift assay showing disruption of the MBNL-CUG repeat interaction by increasing amounts of several small molecules.

FIG. 1C is a graph showing quantitation of the experiments shown in FIG. 1B.

FIG. 1D is a photograph of a gel-shift assay showing several small molecules which do not disrupt the MBNL-CUG repeat interaction.

FIG. 5A is a photograph of a gel showing the inclusion of exon 5 of a cTNT reporter (upper band) in the presence or absence of a $CUG_{960}$ construct in the presence of increasing amounts of pentamidine. The percent of cTNT exon 5 inclusion is shown below the gel.

FIG. 5B is a photograph of a gel showing the inclusion of exon 11 of an insulin receptor (IR) reporter (upper band) in the presence or absence of a $CUG_{960}$ construct in the presence of increasing amounts of pentamidine. The percent of IR exon 11 inclusion is shown below the gel.

SEQUENCE LISTING

Figure 2A:
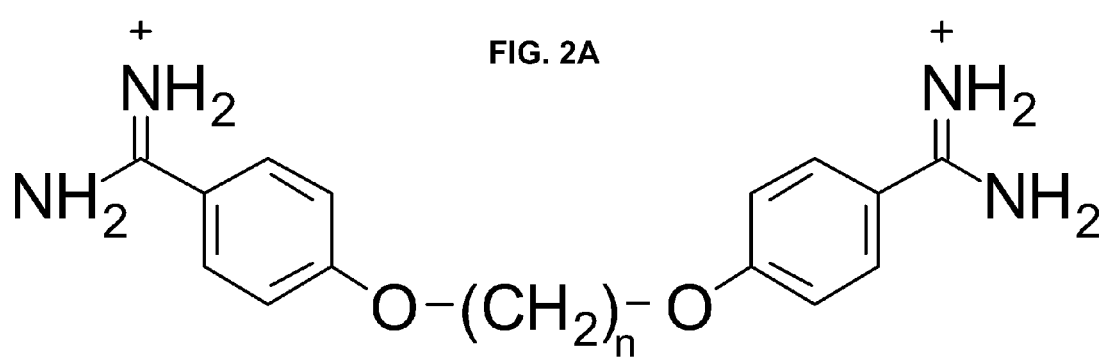
FIG. 2A is the general structure of diamidines, where n=3–10.

Any nucleic acid and amino acid sequences listed herein or in the accompanying sequence listing are shown using standard letter abbreviations for nucleotide bases, and three letter code for amino acids, as defined in 37 C.F.R. 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Aug. 17, 2010, and is 2,801 bytes, which is incorporated by reference herein.

SEQ ID NOs: 1 and 2 show forward and reverse primers, respectively, used to amplify cTNT.

SEQ ID NOs: 3 and 4 show forward and reverse primers, respectively, used to amplify IR.

SEQ ID NOs: 5 and 6 show forward and reverse primers, respectively, used to amplify PLEKHH2.

SEQ ID NOs: 7 and 8 show forward and reverse primers, respectively, used to amplify Clc-1.

SEQ ID NOs: 9 and 10 show forward and reverse primers, respectively, used to amplify Serca1.

DETAILED DESCRIPTION

I. Abbreviations and Terms
  cTNT: cardiac troponin T
  Clc-1: chloride channel 1
  DM: myotonic dystrophy
  DM1: myotonic dystrophy type I
  DM2: myotonic dystrophy type II
  DMPK: dystrophia myotonica-protein kinase gene or protein
  EMG: electromyography
  FRET: fluorescence resonance energy transfer
  FXTAS: fragile X tremor ataxia syndrome
  HDL2: Huntington disease-like 2
  hnRNP H: heterogeneous nuclear ribonucleoprotein H
  IR: insulin receptor
  MBNL: muscleblind-like gene or protein
  PLEKHH2: pleckstrin homology domain containing, family H member 2
  SCA8: spinocerebellar ataxia type 8
  Serca1: sarcoplasmic reticulum/endoplasmic reticulum $Ca^{2+}$ ATPase
  UTR: untranslated region
  ZNF9: zinc finger 9 gene or protein Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety for all purposes. All sequences associated with the GenBank Accession Nos. mentioned herein are incorporated by reference in their entirety as were present on Feb. 20, 2009. In case of conflict, the present specification, including explanations of terms, will control. In addition, the materials, methods, and examples are illustrative only and not intended to be limiting.

Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Derivative: A compound or portion of a compound that is derived from or is theoretically derivable from a parent compound, for example if at least one atom is replaced with another atom or group of atoms. Derivatives also include compounds to which at least one atom or functional group is added or removed, rather than replacing an atom or functional group of the parent compound.

Diamidine: Any of a group of compounds containing two of the groups —C(=NH)NH$_2$ (amidine) or derivatives thereof. The diamidines disclosed herein are bipolar molecules including a lipophilic part including two benzene rings connected by a linker of varying length and a hydrophilic portion including a protonated amidine group attached to each ring. In some examples, the linker may be connected to the benzene rings at the meta or para position relative to the amidine group. In one example, the diamidine is pentamidine, which includes a five carbon linker. Other diamidines include propamidine, butamidine, hexamidine, and heptamidine. Diamidines also include derivatives of diamidines, in which at least one atom is added, removed, or replaced by at least one other atom, or combinations thereof.

A related compound is furamidine and its prodrug pafuramidine. Furamidine contains a single amidine group, rather than two amidine groups.

DMPK: Dystrophia myotonica-protein kinase gene or protein. DMPK is a serine/threonine protein kinase. An expansion of a CUG trinucleotide repeat in the 3' UTR or the last exon of the DMPK pre-mRNA or mRNA causes DM1.

DMPK sequences are publicly available. For example, GenBank Accession numbers NC_000019.8 and NC_000073.5 disclose human and mouse DMPK gene sequences, respectively. GenBank Accession numbers NM_004409.2 and NP_004400.4 disclose exemplary human DMPK cDNA and protein sequences, respectively and GenBank Accession numbers NM_032418.1 and NP_115794.1 disclose exemplary mouse DMPK cDNA and protein sequences, respectively. One skilled in the art will appreciate that DMPK nucleic acid and protein molecules can vary from those publicly available, such as DMPK sequences having one or more substitutions, deletions, insertions, or combinations thereof, while still retaining DMPK biological activity. In addition, DMPK molecules include fragments that retain the desired DMPK biological activity.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. For example, a reference to the DNA molecule that encodes DMPK, or a fragment thereof, encompasses both the sense strand and its reverse complement. Thus, for instance, it is appropriate to generate probes or primers from the reverse complement sequence of the disclosed nucleic acid molecules.

Muscleblind-like (MBNL): Members of the family of muscleblind-like genes or protein. These proteins are double-stranded RNA binding proteins which are pre-mRNA alternative splicing factors. MBNL (MBNL1) is the founding member of the family, which includes MBLL (MBNL2) and MBXL (MBNL3) in both mice and humans. MBNL, MBLL, and MBXL have each been shown to co-localize to nuclear foci with expanded CUG repeats in DM1 cells and expanded CCUG repeats in DM2 cells (Fardaei et al., *Hum. Mol. Gen.* 11:805-814, 2002).

MBNL (MBNL1) sequences are publicly available. For example, GenBank Accession numbers NC_000003.10 and NC_000069.5 disclose human and mouse MBNL gene sequences, respectively. GenBank Accession numbers NM_021038.3 and NP_066368.2 disclose exemplary human MBNL cDNA and protein sequences, respectively and GenBank Accession numbers NM_020007.3 and NP_064391.2 disclose exemplary mouse MBNL cDNA and protein sequences, respectively. One skilled in the art will appreciate that MBNL nucleic acid and protein molecules can vary from those publicly available, such as MBNL sequences having one or more substitutions, deletions, insertions, or combinations thereof, while still retaining MBNL biological activity. In addition, MBNL molecules include alternatively spliced isoforms and fragments that retain the desired MBNL biological activity.

MBLL (MBNL2) sequences are also publicly available. For example, GenBank Accession numbers NC_000013.9 and NC_000080.5 disclose human and mouse MBLL gene sequences, respectively. GenBank Accession numbers NM_144778.2 and NP_659002.1 disclose exemplary human MBLL cDNA and protein sequences, respectively and GenBank Accession numbers NM_175341.4 and NP_780550.1 disclose exemplary mouse MBLL cDNA and protein sequences, respectively. One skilled in the art will appreciate that MBLL nucleic acid and protein molecules can vary from those publicly available, such as MBLL sequences having one or more substitutions, deletions, insertions, or combinations thereof, while still retaining MBLL biological activity. In addition, MBLL molecules include alternatively spliced isoforms and fragments that retain the desired MBLL biological activity.

MBXL (MBNL3) sequences are publicly available. For example, GenBank Accession numbers NC_000023.9 and NC_000086.6 disclose human and mouse MBXL gene sequences, respectively. GenBank Accession numbers NM_018388.2 and NP_060858.2 disclose exemplary human MBXL cDNA and protein sequences, respectively and GenBank Accession numbers NM_134163.4 and NP_598924.1 disclose exemplary mouse MBXL cDNA and protein sequences, respectively. One skilled in the art will appreciate that MBXL nucleic acid and protein molecules can vary from those publicly available, such as MBXL sequences having one or more substitutions, deletions, insertions, or combinations thereof, while still retaining MBXL biological activity. In addition, MBXL molecules include alternatively spliced isoforms and fragments that retain the desired MBXL biological activity.

Myotonic dystrophy: A complex neuromuscular disorder, characterized by myotonia with muscle weakness and wasting, cataracts, cardiac conduction defects, insulin resistance, neuropsychiatric impairment, and other developmental or degenerative manifestations.

Myotonic dystrophy is a disease which is caused by a nucleotide repeat expansion. For example, a CTG nucleotide repeat expansion is present in either the 3' UTR or the last exon of the DMPK gene (DNA) in DM1. Upon transcription of the DMPK gene, a CUG nucleotide repeat expansion is present in the resulting RNA or mRNA. Similarly, a CCTG repeat expansion is present in intron 1 of the ZNF9 gene (DNA) in DM2. Upon transcription, a CCUG nucleotide repeat expansion is present in the resulting ZNF9 RNA transcript, although the expansion is not present in appropriately spliced messenger RNA, where the intron has been removed. Both DM1 and DM2 exhibit similar symptoms.

Nucleotide repeat expansion: A type of mutation in which a set of repeated sequences replicates inaccurately to increase the number of repeats above that normally present in the nucleic acid sequence. Nucleotide repeat expansions include increases in number of trinucleotide, tetranucleotide, and pentanucleotide repeat sequences. The expansions may be present in both DNA and RNA and may be translated or non-translated. In some examples, a nucleotide repeat expansion in a non-coding portion of a RNA molecule produces a toxic RNA, which may result in cellular damage or disease, potentially through a gain-of-function mechanism.

Many nucleotide repeat expansions are associated with disease. For example, trinucleotide repeat expansions in different genes are associated with diseases such as myotonic dystrophy type I (CTG repeat expansion), Fragile X syndrome (CGG repeat expansion), Friedrich ataxia (GAA repeat expansion), Huntington disease (CAG repeat expansion), and several spinocerebellar ataxias (CAG repeat expansions). In other examples of nucleotide repeat expansions associated with disease, a tetranucleotide repeat expansion is associated with myotonic dystrophy type II (CCTG repeat expansion) and a pentanucleotide repeat expansion is associated with spinocerebellar ataxia type 10 (ATTCT repeat expansion).

Figure 2B:
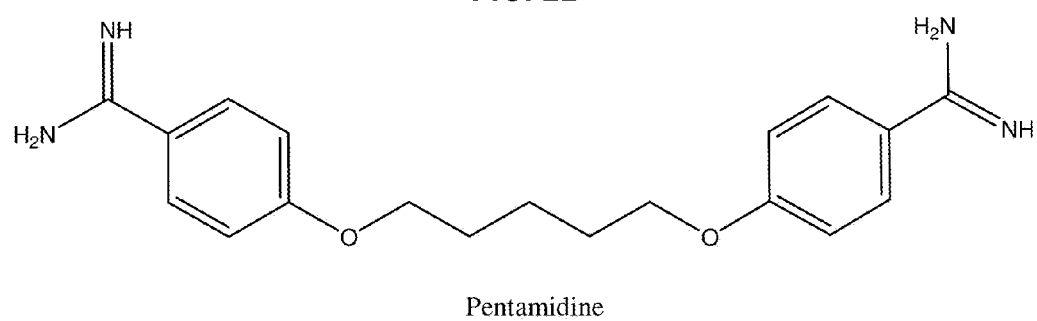
FIG. 2B is the structure of pentamidine.

Pentamidine: A small molecule having the structure $C_{19}H_{24}N_4O_2$ (FIG. 2B). Pentamidine is an FDA-approved drug used to treat *Pneumocystis carinii* pneumonia in AIDS subjects and other immuno-compromised individuals. It is also used to treat Trypanosomiasis and Leishmaniasis. The mechanism of action of pentamidine in these treatments is not known. It is known to bind the minor groove of DNA (Greenridge et al., *Mol. Pharmacol.* 43:982-988, 1993). Pentamidine has also been shown to bind to the NMDA receptor and is neuroprotective in vivo (Reynolds & Aizenman, *J. Neurosci.* 12:970-975, 1992).

Pharmaceutically acceptable vehicle: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more compounds for treatment of myotonic dystrophy, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating: "Preventing" a disease or condition refers to inhibiting the full development of a disease or condition. "Treating" refers to a therapeutic intervention that ameliorates a sign or symptom of a disease or pathological condition after it has begun to develop. "Ameliorating" refers to the reduction in the number or severity of signs or symptoms of a disease or condition. In one embodiment, the disease or condition is myotonic dystrophy.

Prodrug: Any covalently bonded carriers that release a disclosed compound or a parent thereof in vivo when the prodrug is administered to a subject. Prodrugs often have enhanced properties relative to the active agent pharmaceutical, such as solubility and bioavailability. Prodrugs of the disclosed compounds typically are prepared by modifying one or more functional groups present in the compound in such a way that the modifications are cleaved, either in routine manipulation or in vivo, to yield the parent compound. Conventional procedures for the selection and preparation of suitable prodrug derivatives are described, for example, in *Design of Prodrugs*, ed. H. Bundgaard, Elsevier, 1985. In one example, a prodrug is pafuramidine.

RNA (ribonucleic acid): RNA is a long chain polymer which consists of nucleic acids joined by 3'-5' phosphodiester bonds. The repeating units in RNA polymers are four different nucleotides, each of which comprises one of the four bases, adenine, guanine, cytosine, and uracil bound to a ribose sugar to which a phosphate group is attached. In general, DNA is transcribed to RNA by an RNA polymerase. RNA transcribed from a particular gene contains both introns and exons of the corresponding gene; this RNA is also referred to as pre-mRNA. RNA splicing subsequently removes the intron sequences and generates a messenger RNA (mRNA) molecule, which can be translated into a polypeptide. Triplets of nucleotides (referred to as codons) in an mRNA molecule code for each amino acid in a polypeptide, or for a stop signal.

Except where single-strandedness is required by the text herein, RNA molecules, though written to depict only a single strand, encompass both strands of a double-stranded RNA molecule. For example, a CUG repeat sequence includes both single-stranded RNA and double-stranded RNA, such as a stem-loop secondary structure.

Subject: Living multi-cellular vertebrate organisms, a category that includes human and non-human mammals (such as laboratory or veterinary subjects).

Therapeutically effective amount: A dose sufficient to prevent advancement, delay progression, or to cause regression of the disease, or which is capable of reducing symptoms caused by the disease, such as myotonic dystrophy.

Toxic RNA: RNA which contains a non-coding nucleotide repeat expansion and which results in cellular damage or disease. In some instances, toxic RNA may accumulate in the nucleus, sequester binding proteins, and result in abnormal splicing for some pre-mRNAs (Osborne & Thornton, Hum. Mol. Genet. 15:R162-R169, 2006). In a particular example, a CUG trinucleotide repeat expansion in the 3' UTR of the DMPK gene results in production of a toxic RNA which leads to DM1. In another example, a CCUG tetranucleotide repeat expansion in intron 1 of the ZNF9 gene produces a toxic RNA which leads to DM2. Other diseases which may be caused by production of toxic RNA include Fragile X tremor ataxia syndrome (FXTAS), spinocerebellar ataxia type 8 (SCA8), and Huntington disease-like 2 (HDL2).

ZNF9: The zinc finger 9 gene or protein, also known as cellular nucleic acid binding (CNBP) gene or protein. ZNF9 is a nucleic acid binding protein. An expansion of a CCUG tetranucleotide repeat in intron 1 of the ZNF9 pre-mRNA causes DM2.

ZNF9 sequences are publicly available. For example, GenBank Accession numbers NC_000003.10 and NC_000072.5 disclose human and mouse ZNF9 gene sequences, respectively. GenBank Accession numbers NM_003418.1 and NP_003409.1 disclose exemplary human ZNF9 cDNA and protein sequences, respectively and GenBank Accession numbers NM_013493.2 and NP_038521.1 disclose exemplary mouse ZNF9 cDNA and protein sequences, respectively. One skilled in the art will appreciate that ZNF9 nucleic acid and protein molecules can vary from those publicly available, such as ZNF9 sequences having one or more substitutions, deletions, insertions, or combinations thereof, while still retaining ZNF9 biological activity. In addition, ZNF9 molecules include fragments that retain the desired ZNF9 biological activity.

II. Methods of Treating Myotonic Dystrophy

A. Introduction

The current model for DM is that an RNA gain-of-function mechanism is responsible for causing DM, meaning that expansion of the CUG repeats of DMPK or the CCUG repeats of ZNF9 results in an RNA molecule that has a new function, apparently overriding other cellular pathways. The following two pieces of evidence support the RNA gain-of-function model: (1) CUG and CCUG repeats occur in different genes on different chromosomes but both cause DM, and (2) work by Mankodi and colleagues demonstrates that the introduction of CUG repeats within a transgenic mouse is enough to cause some of the symptoms of DM in mice (Mankodi et al., Science 289:1769-1772, 2000). The CUG repeats were inserted within the human skeletal actin gene and this transgene was then expressed in mouse muscle. Mice with long repeats displayed symptoms similar to those of myotonia and myopathy, while mice with short CUG repeats displayed no symptoms, supporting the RNA gain-of-function model for the long CUG repeats.

Transcripts of both DMPK and ZNF9 containing a nucleotide repeat expansion form foci that are retained in the nuclei of DM cells. The proposed mechanism of the gain-of-function model is that the nucleotide repeat expansions bind and sequester specific RNA or DNA binding proteins. The muscleblind-like (MBNL) double-stranded RNA binding protein was found to bind expanded CUG and CCUG repeats in DM1 and DM2 cells (Miller et al., EMBO J. 19:4439-4448, 2000; Fardaei et al., Hum. Mol. Gen. 11:805-814, 2002). In support of the sequestration model of MBNL to the CUG repeats and MBNL's role in DM, a mouse knockout of MBNL results in several of the phenotypes of DM (Kanadia et al., Science 302:1978-1980, 2003). Humans and mice carry two other genes related to MBNL, MBLL and MBXL. Both MBNL and MBLL have been shown to co-localize in vivo with expanded CUG and CCUG repeats (Fardaei et al., Hum. Mol. Gen. 11:805-814, 2002). The founding member of this protein family was first identified in Drosophila, and it was named muscleblind (MBL) because it is required for photoreceptor and muscle development in Drosophila (Begemann et al., Development 124:4321-4331, 1997).

MBNL is not the only splicing factor affected by expanded CUG repeats; the levels of CUG-binding protein (CUG-BP), a single-stranded RNA binding protein, are up-regulated through an unknown mechanism by expanded CUG repeats. CUG-BP and MBNL appear to function antagonistically in regulating splicing, and the amount of each protein in the cell is important (reviewed in Osborne & Thornton, Hum. Mol. Genet. 15:R162-R169, 2006; Ranum & Cooper, Ann. Rev. Neurosci. 29:259-277, 2006). Decreasing and increasing their "active" concentration results in the mis-regulation of alternative splicing of multiple transcripts with an outcome of DM for those who harbor CUG and CCUG expansions.

B. Overview of Several Embodiments

The disclosed methods include methods of treating myotonic dystrophy, comprising administering to a subject a compound that binds a nucleotide repeat expansion in RNA. In some examples, the compound binds to a trinucleotide repeat expansion in RNA or a tetranucleotide repeat expansion in RNA. In some examples, the compounds include a diamidine or a derivative thereof, including but not limited to the compounds described herein (such as compounds 1-15 provided herein). In a particular example, the compound binds to a CUG trinucleotide expansion in RNA, such as a CUG repeat expansion in the pre-mRNA or mRNA of the DMPK gene. In an additional example, the compound binds to a CCUG tetranucleotide repeat expansion in RNA, such as a CCUG repeat expansion in the pre-mRNA of the ZNF9 gene. Also disclosed are methods of treating a disease caused by toxic RNA, comprising administering to a subject a compound that binds a nucleotide repeat expansion in RNA.

The disclosed methods include use of compounds that bind an RNA nucleotide repeat expansion. In some examples, the compound binds to an RNA nucleotide repeat with a $K_d$ from about 0.01 µM to about 100 µM, such as about 0.1 µM to about 75 µM, about 1 µM to about 50 µM, or about 10 µM to about 25 µM. In a particular example, pentamidine binds to a CUG repeat construct with a $K_d$ of about 19 µM.

Methods for determining binding of a compound to an RNA nucleotide repeat expansion are known to those of skill in the art. In one example, binding of a compound to an RNA nucleotide repeat expansion is determined using a fluorescence anisotropy assay. Briefly, an RNA construct consisting of a repeat sequence (such as a CUG repeat or a CCUG repeat) is labeled with a fluorescent compound, e.g., fluorescein, Cy™3, or Cy™5. The labeled RNA construct is incubated with increasing amounts of a compound (such as pentamidine) and fluorescence anisotropy is measured. This method allows quantitation of the interaction of a compound with an RNA nucleotide repeat expansion.

In another example, binding of a compound to an RNA nucleotide repeat expansion may be determined by a gel shift assay (also known as electrophoretic mobility shift assay (EMSA)). A nucleic acid sequence (such as a CUG repeat sequence or a CCUG repeat sequence) is incubated in the presence or absence of a compound or mixture of compounds (such as pentamidine). The nucleic acid sequence is linked to a detectable label, for example a radioactive, fluorescent, chemiluminescent, or biotin label. The samples are separated by polyacrylamide gel electrophoresis and the labeled nucleic acid is detected, with a shift to slower mobility (higher molecular weight) in the presence of the compound compared to nucleic acid in the absence of the compound indicating that the compound binds to the nucleic acid sequence.

An additional method for determining the binding of a compound to an RNA nucleotide repeat expansion is by equilibrium dialysis. The technique of equilibrium dialysis is well known in the art (see e.g., *Handbook of RNA Biochemistry*, Hartmann et al. (eds.), Wiley-VCH, 2005). Briefly, a molecule (such as pentamidine) which is small enough to be dialyzed through a membrane is incubated with a nucleic acid molecule (such as a CUG repeat sequence or a CCUG repeat sequence) which is too large to pass through the membrane. The amount of the compound bound to the RNA is determined by dialyzing free compound through the membrane, while RNA and RNA-compound complexes are retained on the other side of the membrane.

The disclosed methods include methods for treating myotonic dystrophy comprising administering to a subject a compound that binds a nucleotide repeat expansion in RNA. In some examples, the compounds include a diamidine or a derivative thereof, including but not limited to the compounds described herein (such as compounds 1-15 provided herein). In some examples, the compound disrupts binding of a protein to the nucleotide repeat expansion. In one example, the method includes use of a compound that disrupts binding of a protein to CUG repeats of DMPK. In a particular example, the compound disrupts binding of a muscleblind-like protein (such as MBNL, MBLL, or MBXL) to CUG repeats of DMPK. In another example, the method includes use of a compound that disrupts binding of a protein to CCUG repeats of ZNF9. In a particular example, the compound disrupts binding of a muscleblind-like protein (such as MBNL, MBLL, or MBXL) to CCUG repeats of ZNF9. The compound may disrupt binding of additional proteins to RNA nucleotide repeat expansions, such as heterogeneous nuclear ribonucleoprotein H (hnRNP H) or other proteins.

The disclosed methods include use of compositions that disrupt binding of a protein to an RNA nucleotide repeat expansion. In some examples, the composition disrupts binding of a protein to an RNA nucleotide repeat with an $EC_{50}$ from about 1 µM to about 500 µM, such as about 10 µM to about 300 µM, about 25 µM to about 200 µM, or about 50 µM to about 100 µM. In particular examples, pentamidine disrupts binding of MBNL to a CUG repeat construct with an $EC_{50}$ of about 58 µM and disrupts binding of MBNL to a cTNT target construct with an $EC_{50}$ of about 85 µM.

Methods for determining whether a compound disrupts RNA binding activity of a protein to a particular sequence are well known to those of skill in the art. See e.g., *Current Protocols in Molecular Biology*, Ausubel, John Wiley & Sons, 1994; *Molecular Cloning, A Laboratory Manual*, Sambrook et al., Cold Spring Harbor Laboratory, 2001. In one example, binding of a protein to a nucleic acid may be determined by EMSA. A nucleic acid sequence (such as a CUG repeat sequence or a CCUG repeat sequence) is incubated in the presence or absence of a protein or mixture of proteins (such as a muscleblind-like protein). The nucleic acid sequence is linked to a detectable label, for example a radioactive, fluorescent, chemiluminescent, or biotin label. The samples are separated by polyacrylamide gel electrophoresis and the labeled nucleic acid is detected, with a shift to slower mobility (higher molecular weight) in the presence of protein compared to nucleic acid in the absence of protein indicating that a protein in the sample binds to the nucleic acid sequence. To determine whether a compound disrupts the protein-nucleic acid binding, samples containing nucleic acid (such as a CUG repeat expansion or a CCUG repeat expansion) and a binding protein (such as a muscleblind-like protein) are incubated in the presence or absence of a candidate compound. If the compound disrupts the protein-nucleic acid interaction, the shift to slower mobility that is observed in the absence of the compound will not occur or will be reduced compared to the shift in the absence of the compound.

In another example, RNA-protein interaction may be determined using a filter binding assay. Such assays are well known in the art (see, e.g., Hall and Kranz, in *RNA-Protein Interaction Protocols* (Methods in Molecular Biology, volume 118), Humana Press, 1999). Briefly, an RNA (such as a CUG repeat sequence or a CCUG repeat sequence) which is labeled (such as with a radioactive label) is incubated in the presence or absence of a protein or mixture of proteins (such as a muscleblind-like protein). The mixture is then passed over a filter (such as a nitrocellulose filter) and RNA-protein complexes are retained and detected.

RNA-protein interaction may also be assessed utilizing fluorescence resonance energy transfer (FRET). Methods for FRET are well known to those of skill in the art. Briefly, a donor fluorophore is coupled to one molecule (such as an RNA binding protein) and an acceptor fluorophore is coupled to another molecule (such as an RNA, for example a CUG or CCUG nucleotide repeat sequence). If the molecules interact, the fluorophores are brought into proximity, such that an excited donor fluorophore can transfer energy to an acceptor fluorophore, which then emits a particular wavelength. Detection of fluorescence emissions may be made utilizing techniques such as fluorescence microscopy or fluorimetry. One of skill in the art will appreciate that the donor and acceptor fluorophores may be coupled to either the protein or RNA binding partners.

C. RNA Nucleotide Repeat Expansion-Binding Compounds

The disclosed methods utilize compounds that bind RNA nucleotide repeat expansions. In some examples, the compound is a small organic molecule. For example, the compound may include members of the class of diamidines. The diamidines disclosed herein are bipolar molecules including a lipophilic part including two benzene rings connected by a linker of varying length and varying orientation with regard to the benzene ring (such as meta or para), and a hydrophilic portion including a protonated amidine group attached to each ring. For example, compounds for use in the disclosed methods include compounds in which the linker includes a varying number of carbon atoms, such as no carbon atoms to at least ten carbon atoms, for example three to eight carbon atoms. Non-limiting examples include propamidine (three carbon linker), butamidine (four carbon linker), pentamidine (five carbon linker), hexamidine (six carbon linker), heptamidine (seven carbon linker), and octamidine (eight carbon linker). In a particular example, the compound is pentamidine or heptamidine.

Additional diamidine compounds include butenamidine, stilbamidine, and Berenil® (4,4'(diazoamino)dibenzamidine diaceturate).

In another example, the compound is furamidine, or its prodrug, pafuramidine.

Compounds for use in the disclosed methods include derivatives of the compounds described above. Methods for synthesis of derivative compounds are known to those of skill in the art. For instance, the use of derivatives of diamidine compounds is contemplated. In one example, derivatives of pentamidine include, but are not limited to, gamma-oxapentamidine, N-hydroxypentamidine, N,N'-dihydroxypentamidine, and methoxypentamidine.

In some examples, the linker is substituted at the para position of the benzene ring, such as in propamidine, butamidine, pentamidine, hexamidine, heptamidine, octamidine, and so on. In other examples, the carbon linker may be substituted at the meta position of the benzene ring. The linker in either the para- or meta-linked compound may include a variable number of carbon atoms, such as no carbon atoms to at least ten carbon atoms, for example three to eight carbon atoms. In a particular example, the diamidine derivative includes meta-pentamidine, which has the structure:

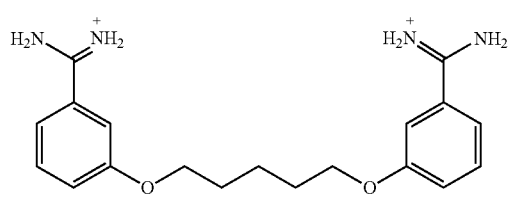

(2)

One of skill in the art will understand that the linker may be at the para and/or the meta position in any of the diamidine derivatives discussed herein.

In some examples, the compound is a diamidine derivative having one or both amidine groups substituted with an ammonium group. The linker may include a variable number of carbon atoms, such as no carbon atoms to at least ten carbon atoms, for example three to eight carbon atoms. In one example, the compound has a five carbon linker (pentamidine), as shown in the following structure:

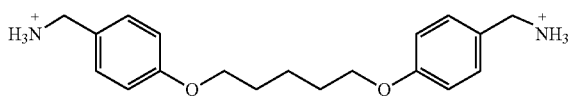

(3)

In other examples, the linker may include one or more atom or functional group that increases solubility of the compound. The linker may include a variable number of carbon atoms, such as no carbon atoms to at least ten carbon atoms, for example three to eight carbon atoms. In a particular example, the compound includes replacing at least one carbon atom in the linker with an oxygen atom. For example, a pentamidine derivative having the third carbon atom replaced with an oxygen atom has the following structure:

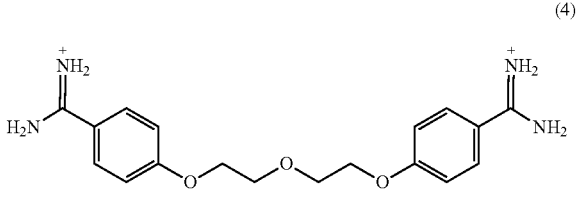 [SMILES: N=C(N)c1ccc(OCCOCCOc2ccc(C(=N)N)cc2)cc1]

(4)

In other examples, the compound may be an octamidine derivative having the third and sixth carbons in the linker replaced with oxygen atoms. In further examples, one or more atom in the linker (such as one or more carbon atom or one or more oxygen atom) may be replaced with a nitrogen atom.

In another example, the compound is a structural isomer of a diamidine (such as pentamidine) wherein the oxygen atoms adjacent to the benzene rings are moved one carbon away from the benzene ring, for example a benzyl ether rather than a phenyl ether. The linker may include a variable number of carbon atoms, such as no carbon atoms to at least ten carbon atoms, for example three to eight carbon atoms. In one example, a structural isomer of pentamidine has the following structure:

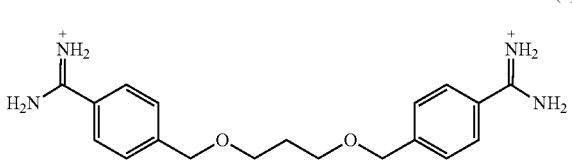

(5)

In further examples, the compound includes one or more atom or functional group in the linker which decreases the flexibility of the linker. The linker may include a variable number of carbon atoms, such as no carbon atoms to at least ten carbon atoms, for example three to eight carbon atoms. In some examples, a benzene ring is substituted in the carbon linker. The benzene ring may be substituted. In a particular example, the compound is a derivative of pentamidine having the structure:

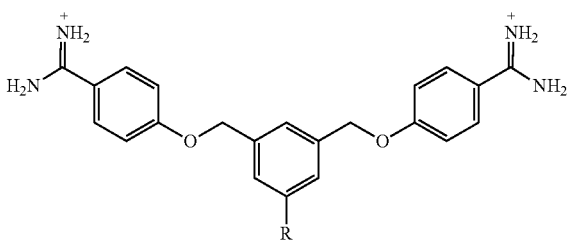

(6)

wherein R includes an electron withdrawing group (EWG, such as a halogen (for example, F or Cl), a carboxylic acid derivative (for example, CN or $CO_2R'$; where R'=alkyl), or other EWG (for example, $CF_3$, $SO_3H$, $CO_2H$, or $NH_3$)), or an electron donating group (EDG, such as an alkyl (for example, $CH_3$), an alcohol (for example, OH), OR', or $NR'_2$; where R'=alkyl).

In other examples, the flexibility of the linker is decreased by including at least one double bond (such as at least one, two, three, four, five, six, seven, or more double bonds). In further examples, the flexibility of the linker is decreased by including at least one triple bond (such as at least one, two, three, four, five, six, seven, or more triple bonds). The linker may include a variable number of carbon atoms, such as no carbon atoms to at least ten carbon atoms, for example three to eight carbon atoms. One of skill in the art will understand that the number of double or triple bonds that can be included is dependent on the length of the carbon linker. An example of a hexamidine derivative which includes two double bonds has the structure:

(7)

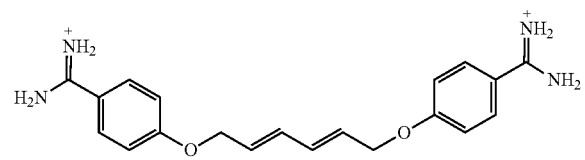

An example of a hexamidine derivative which includes two triple bonds has the structure:

(8)

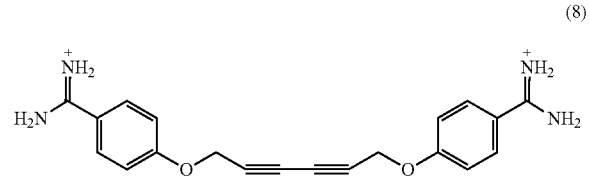 [SMILES: N=C(N)c1ccc(OCC#CC#CCOc2ccc(C(=N)N)cc2)cc1]

In additional examples, the compound includes an oligomer derivative of a diamidine (such as pentamidine or heptamidine), wherein one or more additional unit is attached to the diamidine structure. In some examples, the unit includes a linker, a benzene ring, and an amidine group. The oligomer may include 1 to 10 (such as 1 to 10, for example 1 to 8, 3 to 8, 1 to 6, or 1 to 4) additional units. The linker may include a variable number of carbon atoms, such as no carbon atoms to at least ten carbon atoms, for example three to eight carbon atoms. Oligomers of the diamidine derivatives discussed herein, are also contemplated.

In some examples, the diamidine or diamidine derivative oligomer is a linear oligomer, wherein the additional unit is linked to the benzene ring. The linear oligomer can include three to ten units (such as three, four, five, six, seven, eight, nine, or ten units). In a particular example, the linear oligomer is a trimer. The additional unit may be linked at either the meta or the para position. In a particular example, the additional unit is linked at the meta position, for example, a meta-pentamidine trimer having the structure:

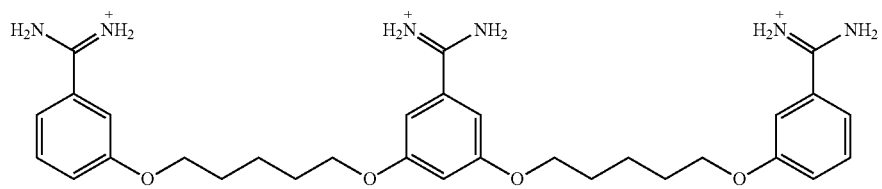

In other examples, the additional unit is linked at the para position, for example, a meta/para pentamidine trimer having the structure:

(10)

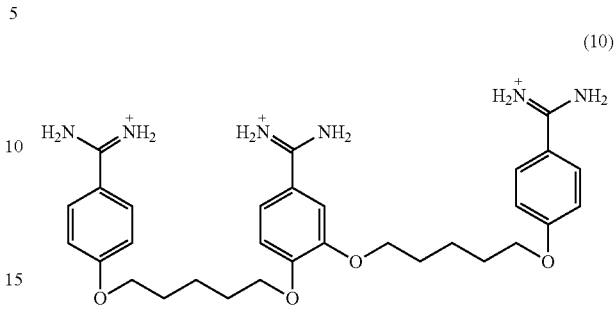

In further examples, the diamidine or diamidine derivative oligomer has a "branched" structure, in which the additional unit is attached via the linker. In a particular example, the oligomer is a branched pentamidine oligomer derivative, having the structure:

(11)

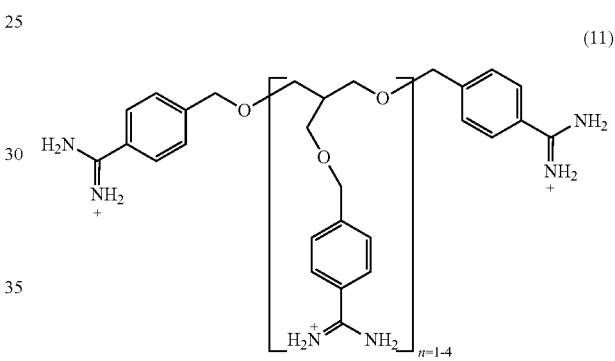

wherein the oligomer includes one to four units in the linker (n=1–4). In other examples, the branched oligomer derivative includes three to ten units, such as three, four, five, six, seven, eight, nine, or ten units.

In some examples, one or more hydrogen atom in the linker is substituted for another atom, such as fluorine. In a particular example, one or more (such as two, four, six, eight, ten, twelve, or more) of the hydrogen atoms are replaced with fluorine. The linker may include a variable number of carbon atoms, such as no carbon atoms to at least ten carbon atoms, for example three to eight carbon atoms. In one example, the derivative is pentamidine with a perfluoroalkyl linker having the structure:

(9)

(12)

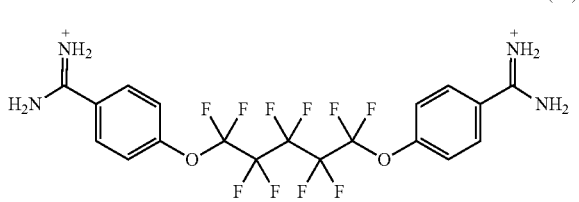

In further examples, the diamidine derivative may be asymmetric, such that the functional groups on each of the benzene rings are different. In one example, the functional groups are differently charged, for example, having a positively charged substituent on one benzene ring (such as an amidine or ammonium) and a negatively charged substituent on the other benzene ring (such as $SO_3^-$, $CO_2^-$, or $PO_3H^-$). The linker may include a variable number of carbon atoms, such as no carbon atoms to at least ten carbon atoms, for example three to eight carbon atoms. In one example, the asymmetric derivative has the structure:

(13)

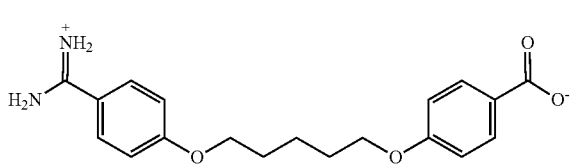

In some examples, the asymmetric derivative may include a supramolecular amidine dimer. In a particular example, a supramolecular amidine dimer has the structure:

(14)

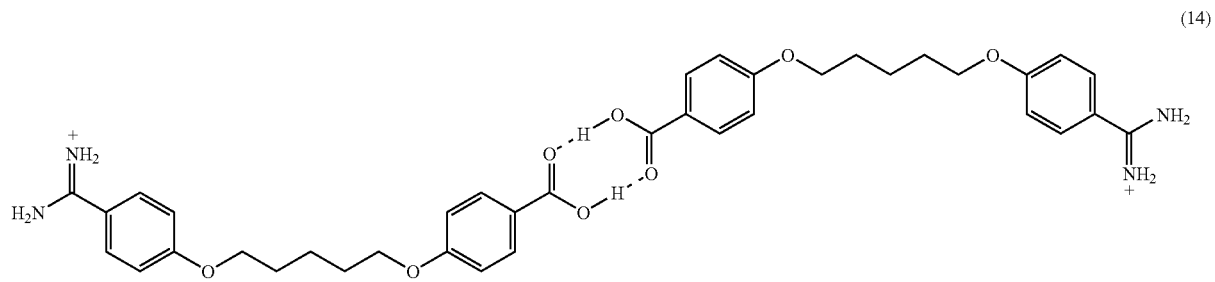

In another example, the asymmetric diamidine derivative may include an arene ring which is highly electron deficient (for example, including F or $CF_3$). In a particular example, the asymmetric derivative having an electron deficient arene ring has the structure:

(15)

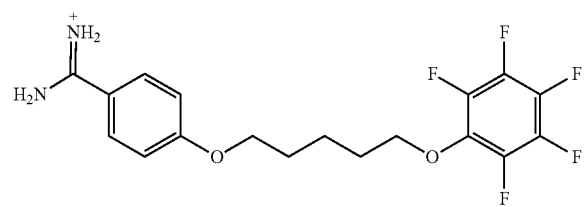

Also contemplated are combinations of the above-described derivatives. One of skill in the art will understand that more than one of the above-described derivatives can be incorporated into a single diamidine derivative compound. For example, one or more of the above-described derivative structures can be introduced in a diamidine derivative having one or more para-linkage.

The contemplated diamidines and diamidine derivatives may be isolated as the chloride salts. However, one of skill in the art will understand that other counterions may be used, including, but not limited to acetate, bromide, and hydrogen sulfate.

Compounds for use in the disclosed methods also include prodrug compounds. A prodrug is any covalently bonded carrier that releases a disclosed compound or a parent thereof in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Conventional procedures for the selection and preparation of suitable prodrug derivatives are described, for example, in *Design of Prodrugs*, ed. H. Bundgaard, Elsevier, 1985. In a particular example, a prodrug includes pafuramidine.

The compounds for use in the disclosed methods can be administered parenterally, i.e., subcutaneously, intramuscularly, intraperitoneally, intrathecally, or intravenously or by means of a needle-free injection device. The compositions for parenteral administration will commonly include a solution of the compound (e.g. pentamidine) in a pharmaceutically acceptable carrier as described above. The composition may also be administered orally, transdermally, sublingually, or by inhalation. Methods for preparing pharmaceutical compositions are known those skilled in the art (see *Remington's Pharmaceutical Sciences*, 15th ed., Mack Publishing Company, Easton, Pa., 1980).

Pharmaceutical compositions including the described compounds can include pharmaceutically acceptable salts of the disclosed compounds. Pharmaceutically acceptable salts of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)

aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms. Description of suitable pharmaceutically acceptable salts can be found in *Handbook of Pharmaceutical Salts, Properties, Selection and Use*, Wiley VCH (2002).

D. Testing of RNA Nucleotide Repeat Expansion-Binding Compounds in Models of DM

The disclosed methods utilize compounds that bind to RNA nucleotide repeat expansions, such as CUG or CCUG repeats, for treating DM. Methods for assessing the usefulness of a compound for treating DM are known to those of skill in the art. For example, compounds may be assessed using models of DM, including cells (such as DM1 or DM2 cells), animal models (such as *Drosophila* or mouse models of DM), or in human subjects having DM1 or DM2.

1. DM Cells

In one example, cells from subjects having DM1 or DM2 or cells from animal models of DM are used to assess compounds which may be used in the disclosed methods. In additional examples, immortalized DM cells may be used. For example, DM1 myoblasts immortalized using SV40 virus may be used (Dansithong et al., *J. Biol. Chem.* 280:5773-5780, 2005) Immortalized cell lines may also be derived from DM2 subjects, or animal models of DM, such as transgenic mouse or *Drosophila* DM models. In further examples, the cells may be non-DM cells (such as HeLa cells) that overexpress an exogenous nucleotide repeat expansion, such as a CUG repeat or CCUG repeat.

DM cells exhibit mis-splicing of pre-mRNA from a number of genes, including cardiac troponin T (cTNT), insulin receptor (IR), muscle-specific chloride channel (CLCN1), sarcoplasmic reticulum/endoplasmic reticulum $Ca^{2+}$ ATPase (SERCA), fast skeletal muscle troponin T (TNNT3), and the striated muscle PDZ-LIM domain protein Cypher/ZASP. The mis-splicing results in the inclusion of one or more exons that are not normally included in an mRNA in normal cells, or the exclusion of one or more exons that are normally included in an mRNA in normal cells. Compounds may be assessed for their ability to decrease or prevent mis-splicing of these or other pre-mRNAs in DM cells. In one example, DM cells (such as DM1 cells, DM2 cells, or cells overexpressing an exogenous nucleotide repeat expansion) are incubated in the presence or absence of test compounds for a period of time (such as about four hours to about 72 hours, for example about 12 hours to about 48 hours, such as about 24 hours). The concentration of the test compound may be varied, such as about 0.1 µM to about 1 mM, for example about 1 µM to about 500 µM, about 25 µM to about 100 µM. Following treatment with the test compound, RNA is isolated and cDNA synthesized (for example using reverse transcriptase, such as Superscript® II (Invitrogen, Carlsbad, Calif.)). Gene-specific primers are used for polymerase chain reaction (PCR) to amplify regions of genes that encompass exons that are mis-spliced in DM cells, such as exon 5 of the cTNT gene or exon 11 of the IR gene. The resulting PCR products may be analyzed by methods well known to one of skill in the art, such as gel electrophoresis and detection of products using labels such as DNA intercalating agents (such as ethidium bromide or SYBR® green) or labels incorporated in the PCR product, including radioactive, fluorescent, bioluminescent, or biotin labels. The effect of a compound on splicing can be determined by quantifying the isoforms (for example using a phosphorimager) and determining the percentage of the mis-spliced isoform produced in the absence and presence of the test compound.

Transcripts containing expanded repeats accumulate in nuclear foci in DM1 and DM2 cells. Muscleblind-like proteins (such as MBNL, MBLL, and MBXL) co-localize with these foci in both DM1 and DM2 cells. The hnRNP H protein also co-localizes to nuclear foci in DM1 and DM2 cells. Compounds may be assessed for their ability to disrupt or prevent co-localization of MBNL or hnRNP H (or other proteins) to nucleotide repeat expansion transcripts in nuclear foci in DM cells (such as DM1 cells, DM2 cells, or cells overexpressing an exogenous nucleotide repeat expansion). In one example, co-localization of a protein to nuclear foci is detected using dual-label fluorescence microscopy utilizing a labeled nucleic acid probe capable of hybridizing to a nucleotide repeat sequence (such as a CUG repeat or CCUG repeat) and a labeled antibody against a protein that co-localizes to the foci (such as MBNL, MBLL, MBXL, or hnRNP H) or a fusion protein including a protein that co-localizes to the foci (such as MBNL, MBLL, MBXL, or hnRNP H) and a fluorescent protein (such as green fluorescent protein or related proteins). Cells are incubated in the presence or absence of test compounds for a period of time (such as about four hours to about 72 hours, for example about 12 to about 48 hours, such as about 24 hours). The concentration of the test compound may be varied, such as about 0.1 µM to about 1 mM, for example about 1 µM to about 500 µM, such as about 25 µM to about 100 µM. The co-localization of proteins with foci is determined in the presence or absence of the test compound to determine whether the compound disrupts or prevents the co-localization.

Compounds may also be assessed for their ability to prevent or inhibit foci formation in DM cells (such as DM1 cells, DM2 cells, or cells overexpressing an exogenous nucleotide repeat expansion). In one example, foci containing nucleotide repeat expansion transcripts can be detected using a nucleic acid probe capable of hybridizing to the repeat sequence. Hybridization can be detected by standard methods; for example, by use of a labeled probe, such as a probe labeled with a fluorescent label. DM cells are incubated in the presence or absence of test compounds for a period of time (such as about four hours to about 72 hours, for example about 12 to about 48 hours, such as about 24 hours). The concentration of the test compound may be varied, such as about 0.1 µM to about 1 mM, for example about 1 µM to about 500 µM, about 25 µM to about 100 µM. The number or size of foci is determined in the presence or absence of the test compound to determine whether the compound prevents or inhibits foci formation.

2. *Drosophila* Model of DM

A *Drosophila* model of DM (DM *Drosophila*) was created by overexpressing a non-coding mRNA containing 480 interrupted CUG repeats of the sequence $[(CUG)_{20}CUCGA]_{24}$ (de Haro et al., *Hum. Mol. Gen.* 15:2138-2145, 2006). DM *Drosophila* expressing the 480 interrupted CUG repeats exhibit progressive muscle degeneration and nuclear foci containing CUG repeat RNA, unlike flies expressing a $(CUG)_{20}$ repeat. DM *Drosophila* expressing the 480 interrupted CUG repeat sequence in the eye also exhibit smaller eyes, disorganization and fusion of the ommatidia, and loss and duplication of the inter-ommatidial bristles.

Compounds may be assessed for their ability to decrease or prevent DM-like phenotypes in a *Drosophila* model of DM. In a particular example, a test compound or mixture is administered orally, such as by mixing with the fly food. Treatment with test compounds may continue for about 1-10 weeks (such as about 1 week to about 4 weeks), or may continue throughout the life of the fly. In one example, a test compound is administered beginning at the larval stage, and continuing throughout the life of the fly. Doses of test compound included in the fly food are from about 1 µM to about 500 µM, such as about 5 µM to about 250 µM, such as about 25 µM to 125 µM.

The phenotype of the DM *Drosophila* is assessed in the presence and absence of treatment with test compound. In one example, skeletal muscle (for example, indirect flight muscles) of *Drosophila* may be sectioned for histological examination. The indirect flight muscles of *Drosophila* expressing the 480 interrupted CUG repeats show vacuolization, loss of muscle fiber organization, and dispersal of nuclei (de Haro et al., 2006). Sections of skeletal muscle from DM *Drosophila* treated with test compounds are compared to untreated DM *Drosophila* to determine whether treatment prevents or decreases the muscle degeneration phenotype. In a particular example, muscle degeneration is measured by assessing the size of vacuoles compared to cell size. DM *Drosophila* are also unable to fly (de Haro et al., 2006), therefore in another example, flies treated with or without test compounds are assessed for their ability to fly and quality or duration of flight. In a further example, *Drosophila* expressing the 480 interrupted CUG repeat sequence in the eye are treated with test compounds to determine whether treatment prevents or decreases the eye disorganization phenotype.

*Drosophila* treated with a test compound or compounds are compared to control flies which are not treated with the compound. Control samples are assigned a relative value of 100%. Treatment with the test compound decreases the DM phenotype when the phenotype relative to the control is about 90%, about 80%, about 70%, about 60%, about 50%, about 25%, or about 0%.

3. Mouse Model of DM

A mouse model of DM has been developed by generating mice that express an expanded CUG repeat (250 repeats) in the 3'UTR of a human skeletal actin transgene (Mankodi et al., *Science* 289:1769-1772, 2000). These mice exhibit myotonia and muscle histopathology consistent with DM (including increases in central nuclei and ring fibers and variability in fiber size), and oxidative muscle fibers.

Compounds may be assessed for their ability to decrease or prevent DM-like phenotypes in a mouse model of DM. In a particular example, a test compound or mixture is administered orally, such as by mixing with distilled water. In another example, a test compound or mixture is administered intraperitoneally, intravenously, such as in saline, distilled water, or other appropriate vehicle. In some examples, treatment with test compound may be a single dose or repeated doses. The test compound may be administered about every 6 hours, about every 12 hours, about every 24 hours (daily), about every 48 hours, about every 72 hours, or about weekly. Treatment with repeated doses may continue for about 1 day to about 10 weeks, such as about 2 days, about 3 days, about 4 days, about 5 days, about 6 days, about 1 week, about 2 weeks, about 4 weeks, about six weeks, about 8 weeks, or about 10 weeks. Doses of test compound are from about 0.1 mg/kg to about 400 mg/kg, such as about 1 mg/kg to about 300 mg/kg, about 2 mg/kg to 200 mg/kg, about 10 mg/kg to about 100 mg/kg, about 20 mg/kg to about 75 mg/kg, or about 25 mg/kg to about 40 mg/kg.

In one example, myotonic discharges of skeletal muscle (such as forelimb muscles or paraspinal muscles) are assessed by electromyography (EMG). EMG recordings are made from DM mice treated with or without test compounds and the number of mice exhibiting myotonic discharges in each group is compared to determine if the test compound inhibits or decreases myotonia in a mouse model of DM. In another example, skeletal muscle histology may be compared between DM mice treated with or without test compound to assess if the test compound inhibits or decreases the muscle pathology of the DM mouse model. In a further example, features of oxidative muscle fibers, such as upregulation of succinate dehydrogenase and cytochrome oxidase are compared between DM mice treated with or without test compounds. In another example, rescue of mis-splicing of RNA (such as cTNT, IR, Clc-1 or Serca1) in mice treated with the test compound is assessed.

Mice treated with a test compound or compounds are compared to control mice which are not treated with the compound. Control samples are assigned a relative value of 100%. Treatment with the test compound decreases the DM phenotype when the phenotype relative to the control is about 90%, about 80%, about 70%, about 60%, about 50%, about 25%, or about 0%.

E. Methods of Treating DM in Human Subjects

The compounds described herein (including, but not limited to, compounds 1-15) may be used to decrease or prevent DM phenotypes in human subjects with DM1 or DM2. In a particular example, a compound or mixture is administered orally, such as by mixing with distilled water. In another example, a test compound or mixture is administered intravenously, such as in saline or distilled water. In some examples, treatment with test compound may be a single dose or repeated doses. The test compound may be administered about every 6 hours, about every 12 hours, about every 24 hours (daily), about every 48 hours, about every 72 hours, or about weekly. Treatment with repeated doses may continue for a period of time, for example for about 1 week to 12 months, such as about 1 week to about 6 months, or about 2 weeks to about 3 months, or about 1 to 2 months. Administration of a compound may also continue indefinitely. Doses of test compound are from about 0.1 mg/kg to about 400 mg/kg, such as about 1 mg/kg to about 300 mg/kg, about 2 mg/kg to 200 mg/kg, about 10 mg/kg to about 100 mg/kg, about 20 mg/kg to about 75 mg/kg, or about 25 mg/kg to about 50 mg/kg.

Methods of assessing DM phenotypes are well known to those of skill in the art. DM phenotypes in affected individuals include muscle weakness (which may lead to foot drop and gait disturbance, as well as difficulty in performing tasks requiring hand dexterity), myotonia (sustained muscle contraction), which often manifests as the inability to quickly release a hand grip (grip myotonia) and which can be demonstrated by tapping a muscle with a reflex hammer (percussion myotonia), and myotonic discharges observed by EMG recording. Pathologic features may be observed by muscle biopsy, including rows of internal nuclei, ring fibers, sarcoplasmic masses, type I fiber atrophy, and increased number of intrafusal muscle fibers.

Changes in DM phenotypes may be monitored in DM subjects following administration of compounds, such as diamidines or derivatives thereof, including, but not limited to pentamidine, heptamidine, and compounds 1-15 disclosed herein. DM phenotypes may be compared to DM subjects who have not received the compounds or comparison may be made to the subject's phenotype prior to administration of the compound in order to assess effectiveness of the compound for treatment of DM.

III. Methods of Treating Toxic RNA Diseases

With the teaching herein that diamidines and derivatives thereof are useful for treating myotonic dystrophy, it will now be understood that these therapies also have broader application in other diseases and conditions caused (or influenced) by toxic RNA, particularly other conditions or diseases that involve nucleotide repeat expansion toxicity. For a review of toxic RNA (or RNA-dominant) diseases, see Osborne and Thornton, Hum. Mol. Genet. 15:R162-R169, 2006. Toxic RNA diseases include those with a mutation in a non-coding region which produce RNAs that have a deleterious gain-of-function effect. In some examples, the mutation is a nucleotide repeat expansion (such as a trinucleotide or tetranucleotide repeat expansion) which is located in an intron or an untranslated region. Without being bound by theory, toxic RNAs may cause pathology by exerting a trans-effect on the alternative splicing of many pre-mRNAs; thus, rather than leading to the production of a mutant protein, they lead to expression of inappropriate splice products in a particular tissue or at a particular developmental stage. In a particular example, CUG repeat expansions, such as in DM1, lead to sequestration of muscleblind-like proteins in ribonuclear foci and depletion in other parts of the nucleoplasm. However, not all toxic RNA diseases are expected to be caused by an identical mechanism.

Myotonic dystrophy is the prototypical toxic RNA disease. Spinocerebellar ataxia type 8 (SCA8) and fragile X tremor ataxia syndrome (FXTAS) are representative additional diseases. SCA8 is caused by CUG repeat expansions in a non-coding RNA (ATXN8OS/SCA8), while in FXTAS there is an expansion of about 70-120 CGG repeats in the 5' UTR of the FMR1 gene. Another toxic RNA disease is Huntington disease-like 2 (HDL2), which is caused by a CUG repeat expansion in an intron or the 3' UTR of the junctophilin 3 gene.

It will be understood that the methods and compositions described herein for treating DM, comprising administering a compound that binds an RNA nucleotide repeat expansion, are applicable to methods of treating toxic RNA diseases, such as those described above. The methods for assessing the effectiveness of test compounds for treating such diseases in cells, appropriate animal models, or affected subjects are known to one of skill in the art. For example, animal models of FXTAS (Jin et al., Neuron 39:739-747, 2003; Brouwer et al., Exp. Cell Res. 313:244-253, 2007) and SCA8 (Mutsuddi et al., Curr. Biol. 14:302-308, 2004; Moseley et al., Nature Genet. 38:758-769, 2006) are known to those in the art.

The present disclosure is illustrated by the following non-limiting Examples.

EXAMPLES

Example 1

Identification of Small Molecules that Disrupt MBNL-RNA Interaction

This example describes the identification of small molecules that disrupt an MBNL-CUG RNA complex.

Cloning and Protein Purification

MBNL1 (MBNL) was PCR amplified and was cloned into GST fusion vector pGEX-6P-1 (GE Healthcare, Piscataway, N.J.), using DNA encoding a MBNL isoform with amino acids 1-382). Both the full length MBNL and MBNL (1-260) constructs were cloned using BamHI and NotI restriction sites. Using BL21-Star expression cells (Invitrogen, Carlsbad, Calif.), protein expression was induced with 0.25 mM IPTG at an $OD_{600}$ of about 0.5-1, for 3-4 hours at 37° C. Cells were lysed in 30 ml of buffer (500 mM NaCl, 25 mM Tris pH 7.5, 10 mM β-mercaptoethanol (BME) and 5% glycerol) using 1 mg/ml of lysozyme, followed by sonication (3×30 seconds). Cell extract was centrifuged for 15 minutes at 17,000 rpm, and lysate which contained GST-MBNL was collected. GST-MBNL was bound to GST affinity beads for 30 minutes at 4° C. Beads were washed 5 times with buffer (1M NaCl, 25 mM Tris pH 7.5 and 5 mM BME); MBNL was cleaved from the affinity tag with Precision Protease (Amersham) and collected from the beads. The protein was then run over an anion exchange (Q) column. Co-purifying contaminants bind the column, but MBNL does not. MBNL was collected in the column flow through, concentrated and dialyzed into storage buffer (30% glycerol, 300 mM NaCl, 20 mM Tris pH 7.5, 5 mM BME) and stored at −80° C. Aliquots were removed from −80° C. and temporarily placed at −20° C. until used for an experiment.

RNA Labeling and Purification

All RNA substrates that were radiolabeled were ordered from IDT DNA (Coralville, Iowa), and 5' end-labeled using $[\gamma^{-32}P]$ATP. All radiolabeled RNAs were purified on 8% polyacrylamide denaturing gels.

Gel Shift Assay

Solutions for the protein-RNA binding experiments contained 125 mM NaCl, 5 mM $MgCl_2$, 20 mM Tris (pH 7.5), 7.5% glycerol, 2 mg/ml bovine serum albumin, and 0.1 mg/ml heparin. Prior to incubation, RNA substrates were annealed by incubation at 95° C. for 2 minutes and then placed directly on ice for 20 minutes in 66 mM NaCl, 6.7 mM $MgCl_2$, and 27 mM Tris (pH 7.5). Protein was then added to the RNA in the presence or absence of the small molecule. The binding reaction was carried out in a 10 μL volume and was incubated for 10 minutes at room temperature before 2-4 μL were loaded on a pre-chilled 4° C. gel. RNA and RNA-protein complexes were separated on 3% acrylamide (37.5:1), 0.3% agarose (low melting point), 0.5× Tris-Borate (TB) gels, run for approximately 2-3 hours at 4° C. at 25-50 volts. Gels were dried and autoradiographed. For the neomycin B and $CUG_8$ gel shift, an 8% acrylamide (29:1), 0.5×TB gel was used and run for 3 hours at 4° C. at 175 volts. All small molecules were dissolved in either water or ethanol, according to the manufacturer's guidance for solubility.

For binding curves, gels were quantified using ImageQuant® software (Molecular Dynamics, Piscataway, N.J.). The percent RNA bound was determined by taking the ratio of RNA-protein complex to total RNA, per lane. Any counts in the well were discarded as it was unapparent if the RNA was bound by protein, small molecule or was in an aggregate. Binding curves were graphed using KaleidaGraph software (Synergy Software, Reading, Pa.). For the neomycin B and $CUG_8$ gel shift, the apparent $K_d$ was determined using Equation 1, where Y=fraction bound, m0=small molecule concentration, m1=total RNA concentration, and m2=$K_d$.

$$Y = \left[ (m0 + m1 + m2) - \sqrt{(\{-m0 - m1 - m2\}^2 - 4 \times m0 \times m1)} \right] / 2 \times m1 \quad \text{Equation 1}$$

For determining the $K_d$ of a small molecule for $CUG_4$ when competing with MBNL, Equation 2 was used that takes the competing ligand (MBNL) and its affinity for the competition target (the RNA) into account, where Y=fraction bound, m0=MBNL concentration, m1=total RNA concentration, m2=MBNL's $K_d$ for RNA target, m3=small molecule concentration, and m4=small molecule's $K_d$ for RNA target.

$$Y = \left[\left(m0 + m1 + m2 + \left[\frac{m2 \times m3}{m4}\right]\right) - \sqrt{\left(\left\{-m0 - m1 - m2 - \left[\frac{m2 \times m3}{m4}\right]\right\}^2 - 4 \times m0 * m1\right)}\right] \Big/ 2 \times m1$$

Equation 2

For determining the $EC_{50}$, Equation 3 was used, where m0=small molecule concentration, m1=$EC_{50}$, m2=Hill coefficient, and m3=fraction MBNL bound without small molecule present.

$$Y = m3/[1+(m0/m1)^{m2}]$$

Equation 3

Results

Small molecules known to bind nucleic acids were screened for their ability to disrupt MBNL-RNA interactions. FIG. 1A shows the gel-shift that occurs on incubation of MBNL protein with a short RNA CUG repeat. Four compounds were identified that disrupt the MBNL-CUG interaction at micromolar concentrations: pentamidine, neomycin B, thiazole orange, and ethidium bromide (FIG. 1B). Pentamidine was able to disrupt the interaction at lower concentrations than the other small molecules tested, exhibiting an $EC_{50}$ of 58 μM under the conditions tested (FIG. 1C). In contrast, actinomycin D, kanamycin, and paromomycin did not disrupt the MBNL-CUG interaction at any concentration (FIG. 1C). The structure of a general diamidine compound is shown in FIG. 2A and the structures of pentamidine and the related compound propamidine are shown in FIG. 2B.

Example 2

Characterization of Pentamidine-RNA Binding

This example describes the characteristics of pentamidine binding to RNA and its ability to disrupt MBNL-RNA binding interactions.

Fluorescence Anisotropy

Fluorescent RNAs were ordered from Dharmacon RNA Technologies (Lafayette, Colo.), and deprotected according to the manufacturer's protocol. RNA was snap annealed in 175 mM NaCl, 20 mM Tris pH 7.5, 5 mM $MgCl_2$. All fluorescence anisotropy experiments were performed in this buffer, with the addition of 0.1 mg/ml of heparin when using protein. Experiments were performed at 25° C. in a 7.5 mm wide Spectrosil® far UV quartz cuvette (Starna Cells, Inc, Atascadero, Calif.), using an L-format FluoroMax®-3 fluorimeter (Horiba Jobin Yvon, Inc., Edison, N.J.). Each anisotropy run was normalized by setting the initial value of the anisotropy of the RNA alone to zero, which converts the data into Δ anisotropy. Curves were graphed using KaleidaGraph (Synergy) software. For curve fitting of titrations and determining apparent $K_d$ values, Equation 1 was used (Example 1). The error bars on the binding curve were obtained by averaging individual titration points from three separate experiments and calculating the standard deviation.

Results

Figure 3B:
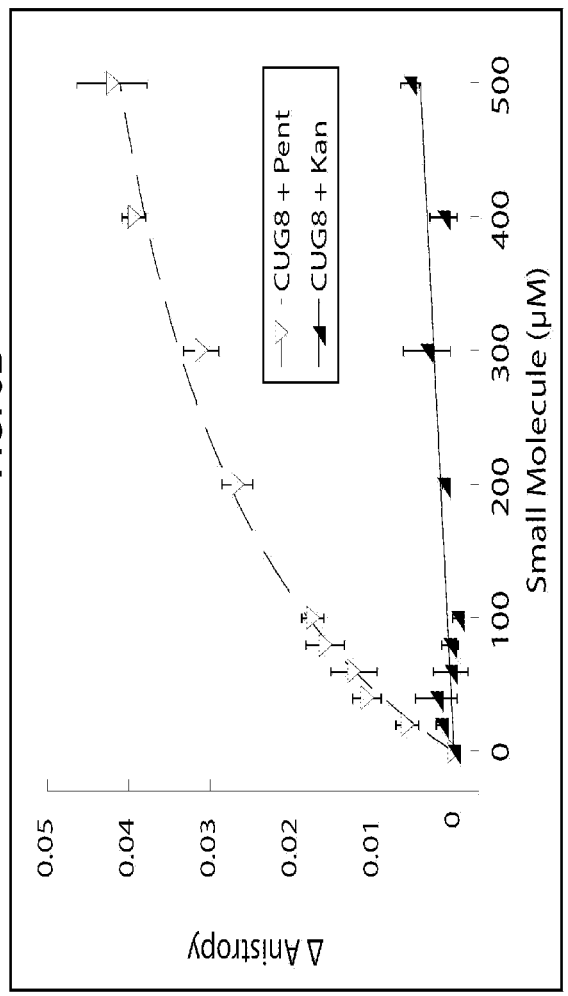
FIG. 3B is a graph showing quantitation of interaction of small molecules with a fluorescently labeled CUG repeat construct. Pent, pentamidine; Kan, kanamycin.
Figure 3A:
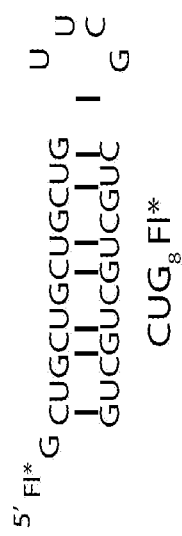
FIG. 3A is the CUG repeat structure used in fluorescence anisotropy experiments. The 5' end of the RNA is labeled with fluorescein.

To determine if pentamidine binds to the CUG repeats and not to MBNL, fluorescein labeled CUG repeats (FIG. 3A) were used to monitor the binding of pentamidine directly to the CUG repeats in the absence of MBNL. As shown in FIG. 3B, there was a change in fluorescence anisotropy as pentamidine was added, showing pentamidine binds the CUG repeats. Quantifying this interaction revealed that pentamidine bound the CUG repeats with a $K_d$ of 19 μM under these conditions.

Figure 4A:
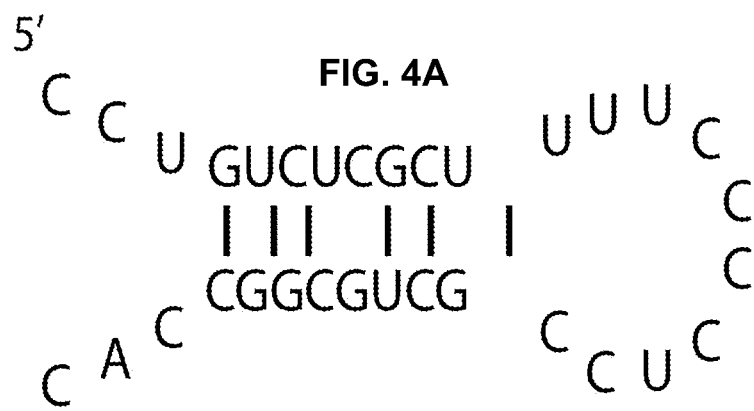
FIG. 4A is the structure of the MBNL binding site in the cardiac troponin T (cTNT) pre-mRNA.
Figure 4B:
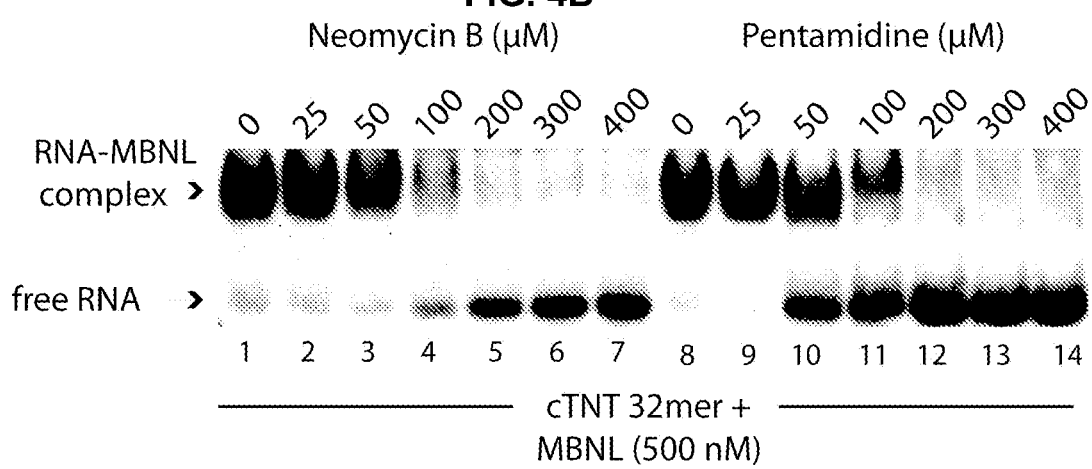
FIG. 4B is a photograph of a gel-shift assay showing disruption of the MBNL-cTNT interaction by increasing amounts of neomycin B and pentamidine.
Figure 4C:
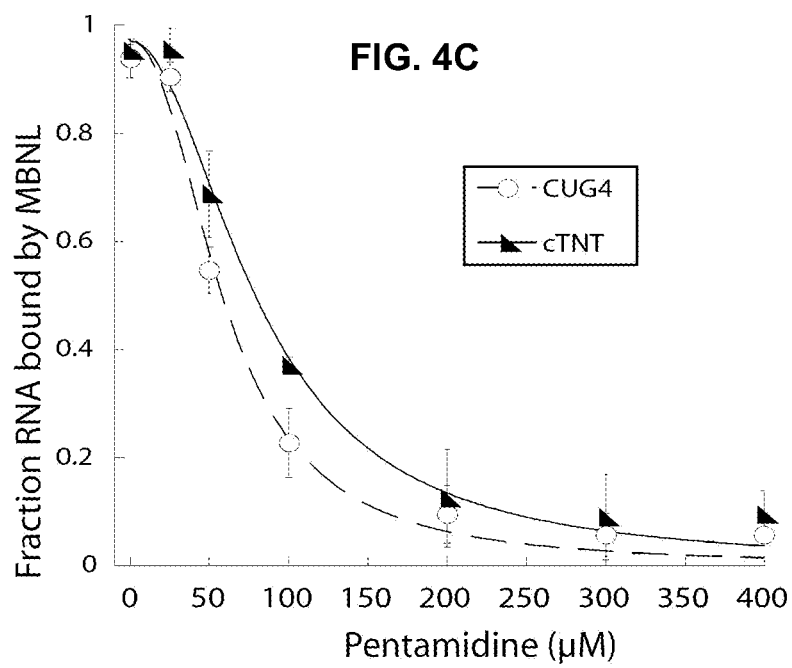
FIG. 4C is a graph quantitating disruption of the MBNL-CUG repeat interaction (CUG4) and the MBNL-cTNT interaction (cTNT) by pentamidine.

Pentamidine has been shown previously to bind to other RNAs and DNAs (Zhang et al., RNA 6:937-951, 2000); therefore, we determined pentamidine binding to an endogenous target of MBNL. The endogenous MBNL RNA target within the cardiac troponin T (cTNT) pre-mRNA (FIG. 4A) was used to assess the ability of pentamidine to disrupt the MBNL-cTNT interaction. Pentamidine modestly inhibited the MBNL-CUG interaction more strongly compared to the MBNL-cTNT interaction (FIGS. 4B and C). Pentamidine showed an $EC_{50}$ of 58 μM for MBNL-CUG versus an $EC_{50}$ of 85 μM for MBNL-cTNT. In contrast, neomycin B, which also disrupts MBNL-CUG interactions, bound the cTNT site with stronger affinity compared to the CUG repeats ($EC_{50}$ of 50 μM versus 110 μM, respectively).

Example 3

Effects of Diamidines on RNA Splicing

This example describes assays characterizing the effect of diamidines on RNA splicing. Diamidines correct splicing defects in a cell-based model of DM utilizing expression of a 960 CUG repeat plasmid.

In Vivo Splicing

HeLa cells were grown in monolayers in DMEM with GlutaMAX™ (Gibco, Carlsbad, Calif.) and supplemented with 10% fetal bovine serum. Approximately 2.0 (±0.2)×$10^5$ cells were plated in 6 well plates and transfected 18-20 hours later at 70-90% confluency. 1 μg of plasmid was transfected into each well of cells, using 5 μL of Lipofectin® 2000 (Invitrogen) according to the manufacturer's protocols. For co-transfection, 1 μg of total plasmid was transfected, at 500 ng of each construct. Test compounds were added 4 hours after transfection, when the media was changed. Cells were harvested 18-22 hours after transfection using TrypLE™ reagent (Gibco).

Immediately following harvesting, RNA was isolated from the cell pellets using an RNeasy® kit (Qiagen, Valencia, Calif.). 500 ng of isolated RNA was DNased with RQI DNase (Promega, Madison, Wis.) according to manufacture's protocol. 100 ng of DNAsed RNA was reverse transcribed with Superscript® II (Invitrogen, Carlsbad, Calif.) and a cTNT-specific reverse primer according to manufacturer's protocols. 30 ng of the reverse transcription reaction was subjected to 22-25 rounds of PCR amplification using cTNT specific primers spiked with a forward primer 5' end-labeled with [γ-$^{32}$P]ATP. Similar methods were used to reverse transcribe and amplify IR and PLEKHH2. The linear range for PCR was determined for the cTNT and the IR constructs and found to be between 20-26 cycles. The resulting PCR products were run on a 6% (19:1) polyacrylamide denaturing gel. The gel was subsequently autoradiographed and quantitation of the radioactive bands was performed using ImageQuant® software.

The following primer pairs were used. For the cTNT minigene, the forward primer was GTTCACAACCATCTAAAG-CAAGATG (SEQ ID NO: 1), and the reverse primer was GTTGCATGGCTGGTGCAGG (SEQ ID NO: 2). For the IR minigene, the forward primer was GTACAAGCTTGAAT-GCTGCTCCTGTCCAAGACAG (SEQ ID NO: 3), and the reverse primer was GCCCTCGAGCGTGGGCACGCTG-GTC (SEQ ID NO: 4). The underlined sections are for cloning purposes. For the PLEKHH2 minigene, the forward primer was CGGGGTACCAAATGCTGCAGTTGACTCTCC (SEQ ID NO: 5), and the reverse primer was CCGCTCGAGCCATTCATGAAGTGCACAGG (SEQ ID NO: 6).

Results

Figure 5C:
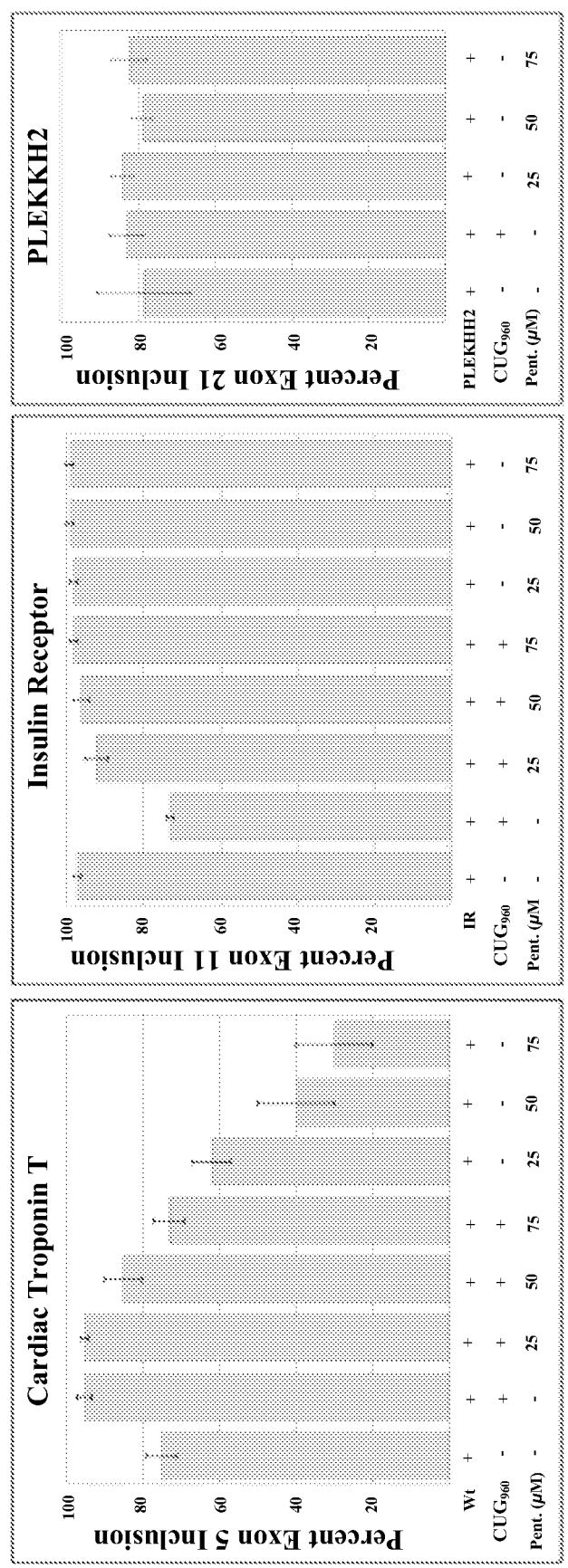
FIG. 5C is a series of histograms showing percent exon inclusion for cTNT, IR, or pleckstrin homology domain containing, family H member 2 (PLEKHH2) in the presence or absence of a $CUG_{960}$ construct in the presence of increasing amounts of pentamidine.

The ability of pentamidine to alter the splicing defects observed in a cell-based model for DM was tested. This was accomplished in a system using cells transformed with a plasmid expressing 960 CUG repeats where the expression of these CUG repeats causes splicing defects similar to those observed in DM cells and DM subjects (Savkur et al., Nature Genet. 29:40-47, 2001). Using this 960 CUG repeat plasmid and splicing reporters in HeLa cells an assay was developed in which the addition of the repeats alter the splicing patterns of the reporters. The addition of pentamidine to the cells expressing CUG repeats reversed the effect of the 960 CUG repeats. This reversal by pentamidine occurred for both cTNT and IR splicing reporters (FIGS. 5A and B). The effect of pentamidine was dose dependent for both reporters. At 75 µM pentamidine, there was full recovery for the inclusion of exon 5 in the cTNT reporter, while 50 µM pentamidine showed partial rescue and 25 µM pentamidine had no effect (FIGS. 5A and 5C). For the IR reporter, the mis-splicing was partially rescued at 25 µM pentamidine and fully rescued at 50 µM pentamidine (FIGS. 5B and 5C).

To determine if pentamidine affects splicing in the absence of the CUG repeats, pentamidine was added to the cells containing the splicing reporters but lacking the CUG repeats (FIG. 5A-C). The addition of pentamidine did not affect the splicing of the IR reporter (FIGS. 5B and 5C), but did affect splicing of the cTNT splicing reporter (FIGS. 5A and 5C). In the absence of CUG repeats, pentamidine had a greater effect on the splicing of the cTNT minigene than in the presence of CUG repeats (FIGS. 5A and 5C). At 25 µM pentamidine, exon 5 was reduced to 62% inclusion, while 75 µM pentamidine reduced exon 5 inclusion to 30%. Pentamidine binds the same stem-loop that MBNL binds within intron 4 of the cTNT pre-mRNA, suggesting that MBNL and pentamidine repress exon 5 inclusion by inhibiting recognition of the 3' splice site.

To test the effect of pentamidine on splicing more generally, the splicing of a PLEKHH2 minigene that contains exons 20-22 was tested in the presence of pentamidine. Splicing was unchanged by the addition of either pentamidine or expression of the CUG repeats (FIG. 5C). This suggests that pentamidine is not a general inhibitor of pre-mRNA splicing.

Figure 6:
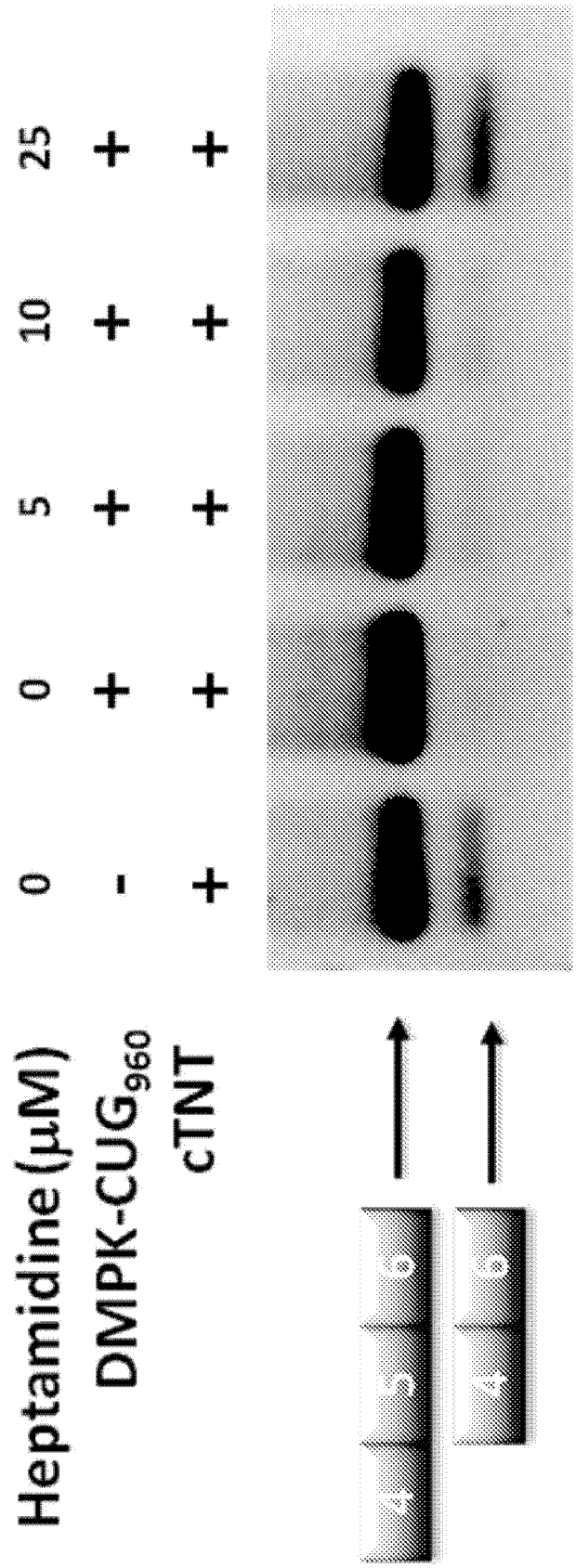
FIG. 6 is a photograph of a gel showing the inclusion of exon 5 of a cTNT reporter (upper band) in the presence or absence of a $CUG_{960}$ construct in the presence of increasing amounts of heptamidine.

The ability of heptamidine to alter splicing defects was also tested. The addition of heptamidine to the cells expressing CUG repeats reversed the effect of the 960 CUG repeats on splicing of the cTNT reporter construct. Heptamidine completely rescued cTNT missplicing in the presence of the $CUG_{960}$ construct at 25 µM (FIG. 6). In contrast, complete rescue of cTNT splicing required 75 µM pentamidine.

Example 4

Effects of Pentamidine on Sequestration of MBNL to Nuclear Foci

This example describes assays characterizing the effect of pentamidine on sequestration of MBNL to nuclear foci. Pentamidine relieves MBNL sequestration in a cell-based model of DM utilizing expression of a 960 CUG repeat plasmid.

Methods

HeLa cells were plated in 6 well plates onto coverslips pre-treated with poly-L-lysine. Cells were transfected as described in Example 3. For transfection, 50 ng of MBNL-eGFP plasmid and 500 ng of $CUG_{960}$ plasmid were transfected for each experiment. A total of 1 µg of plasmid DNA was transfected, with the additional amount being empty pcDNA3 vector. After transfection, pentamidine was added and the cells were fixed 16 hours later.

Cells were fixed for 15 min at room temperature (RT) with 4% paraformaldehyde and washed 5 times for 2 min in 1×PBS at RT. Cells were stored at 4° C., if not probed immediately. For fluorescence in situ hybridization, cells were permeabilized with 2% pre-chilled acetone in 1×PBS, at RT for 5 min. Cells were pre-washed with 30% formamide, 2×SSC for 10 min at RT. Cells were then probed for 2 hours at 37° C., with 1 ng/µl Cy3 $CAG_{10}$ probe (Integrated DNA Technologies, Coralville, Iowa) in 30% formamide, 2×SSC, 0.02% BSA, 66 µg/ml yeast tRNA, 2 mM vanadyl complex. The cells were washed for 30 min in 30% formamide, 2×SSC at 42° C., then with 1×SSC for 30 min at RT. The cells were mounted onto glass slides using Vectashield HardSet mounting medium with DAPI (Vector Laboratories, Burlingame, Calif.). Cells were imaged on an Axioplan compound microscope (Carl Zeiss, Thornwood, N.Y.) and pictures taken with a Coolpix 990 camera (Nikon, Melville N.Y.). MBNL-eGFP was visualized using GFP fluorescence, exciting from 450-490 nm and visualizing at 520 nm. Multiple image files were merged using ImageJ (NIH).

Cells were scored by eye with the following criteria. Foci were considered punctate if there were few (about 8 or less) foci per cell with very little area in the nucleus stained. Foci were considered diffuse if a large area of the nucleus was stained (>50%), with few or no visible foci. Foci were considered intermediate if staining of the nucleus was broader than punctate, but distinct foci were discernable. 201 cells were scored for the MBNL-GFP and $CUG_{960}$ double transfection. 242 cells treated with pentamidine (50 µM) were scored. A chi test with two degrees of freedom was performed.

Results

Figures 7A, 7P:
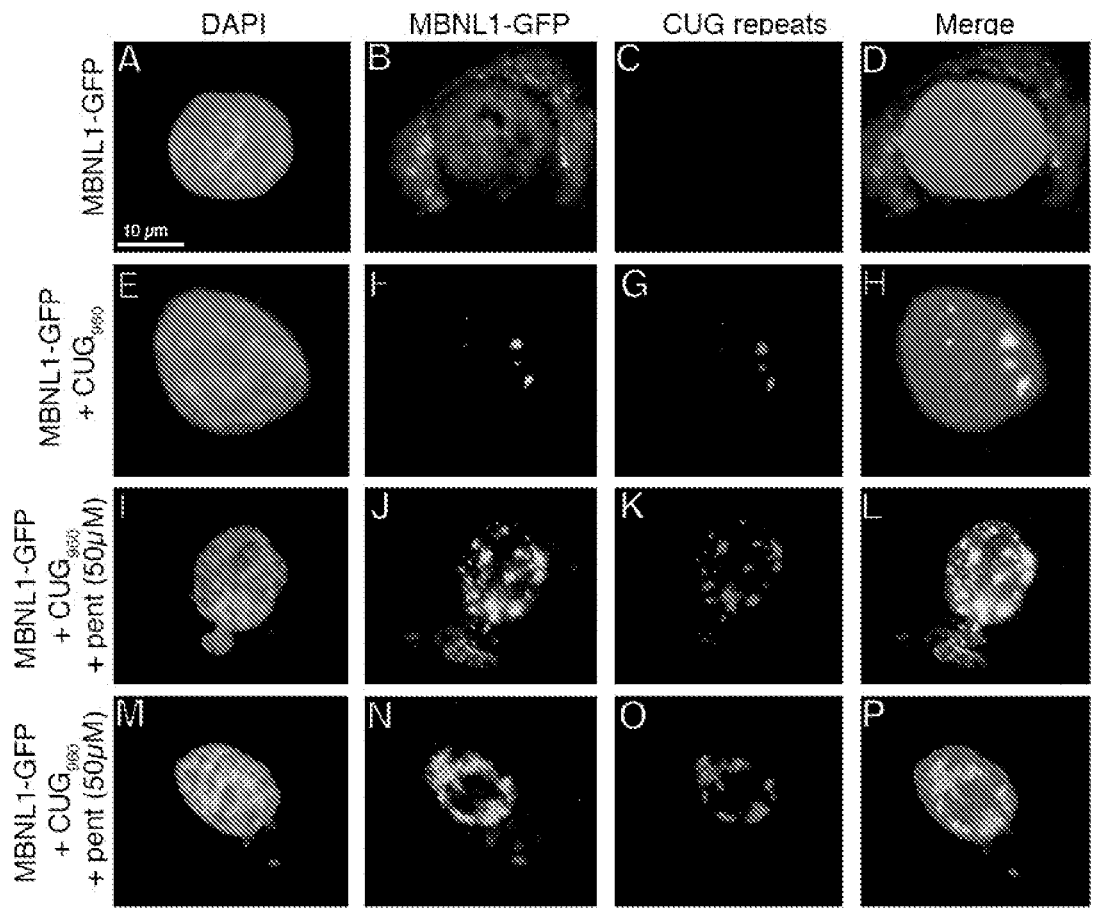
FIG. 7 is a series of photomicrographs showing staining of HeLa cells transfected with MBNL-GFP (A-D) or MBNL-GFP and $CUG_{960}$ construct (E-P) with or without 50 μM pentamidine. Cells were stained with the nuclear stain DAPI (A, E, I, M) or Cy3 $CAG_{10}$ probe (C, G, K, O) and imaged using an Axioplan compound microscope. Merged images from MBNL1-GFP and CUG repeats are shown in parts D, H, L, and P.
FIG. 7Q is a histogram showing the percentage of cells with particular foci characteristics in cells containing MBNL-GFP and $CUG_{960}$ with or without the addition of 50 μM pentamidine.
Figure 7Q:
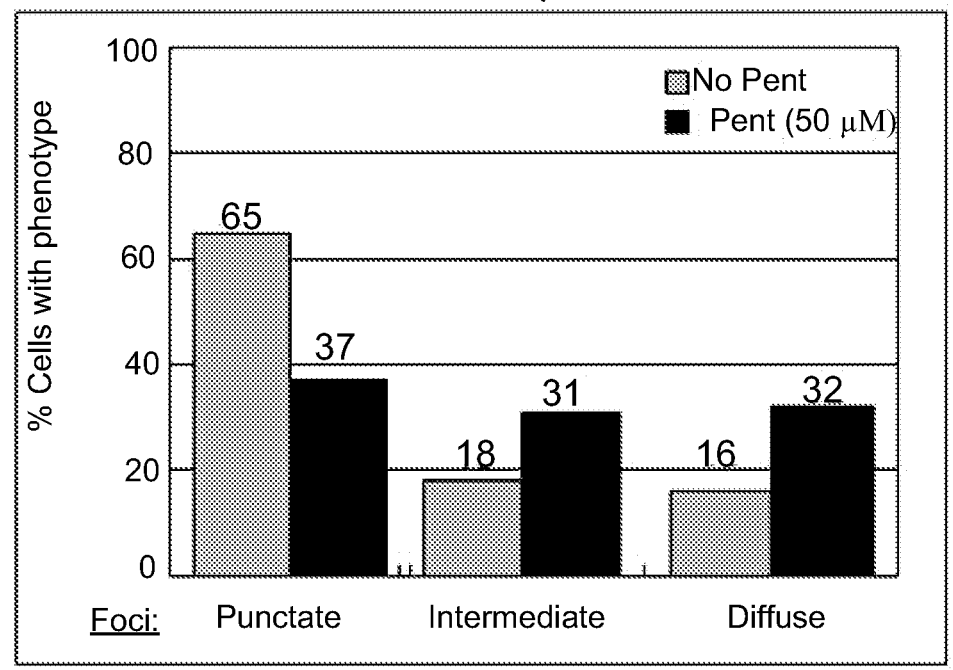

To directly visualize the effect of pentamidine on MBNL sequestration, CUG foci formation was investigated in the presence and absence of the small molecule. A MBNL-GFP fusion protein co-localizes with $CUG_{960}$ repeat RNA when both constructs are transfected into HeLa cells (FIG. 7A-H). Upon the addition of pentamidine, the co-localization of MBNL, as well as the characteristics of the CUG RNA in the foci was changed (FIG. 7I-P). The most significant effect observed was the change in the RNA portion of the foci. With just MBNL-GFP and $CUG_{960}$ present, the foci were small and punctate and did not stain a large portion of the nucleus (FIG. 7G). However, upon the addition of pentamidine, the foci became increasingly more diffuse (FIGS. 7K and 7O). To quantify this difference in foci formation, foci characteristics in cells containing MBNL-GFP and $CUG_{960}$ with or without the addition of pentamidine (50 µM) were scored (FIG. 7Q). The foci were scored as punctate, diffuse, or intermediate (if the cell contained a mixture of punctate and diffuse foci). Representative foci can be seen in FIG. 7: punctate foci (panel 7G), intermediate foci containing moderate surface area staining, although discernable foci could still be seen (panel 7K), and diffuse foci, with broad staining and no specific foci are seen (panel 7O). A chi test comparing these two populations (with or without pentamidine) has a p-value of $1.8 \times 10^{-8}$, demonstrating that the difference between these populations is significant.

The co-localization of MBNL with the CUG RNA was difficult to score, as the MBNL-GFP signal was consistently low (as only 50 ng of plasmid was transfected to avoid substantial amounts of additional MBNL from being sequestered to the foci beyond endogenous levels). The signal could not be significantly amplified with a primary antibody probe against GFP. The MBNL-GFP fusion protein was observed to stain for both the nucleus and the cytoplasm when it was transfected alone (FIG. 7B). The addition of CUG repeats resulted in the commonly observed sequestration of nearly all of the MBNL1 to the foci (FIG. 7F). Upon the addition of pentamidine, MBNL sequestration was partially relieved in many cells, with the protein regaining some diffuse staining throughout the cell, although much of the MBNL signal still co-localized with the CUG RNA (FIGS. 7J and 7N). This suggests that a partial release of the sequestered MBNL1 occurred at 50 µM pentamidine, which apparently is enough to partially rescue the cTNT mis-splicing and fully rescue the IR mis-splicing (as described in Example 3).

Example 5

Effect of Pentamidine in a Mouse Model of DM

Figure 8A:
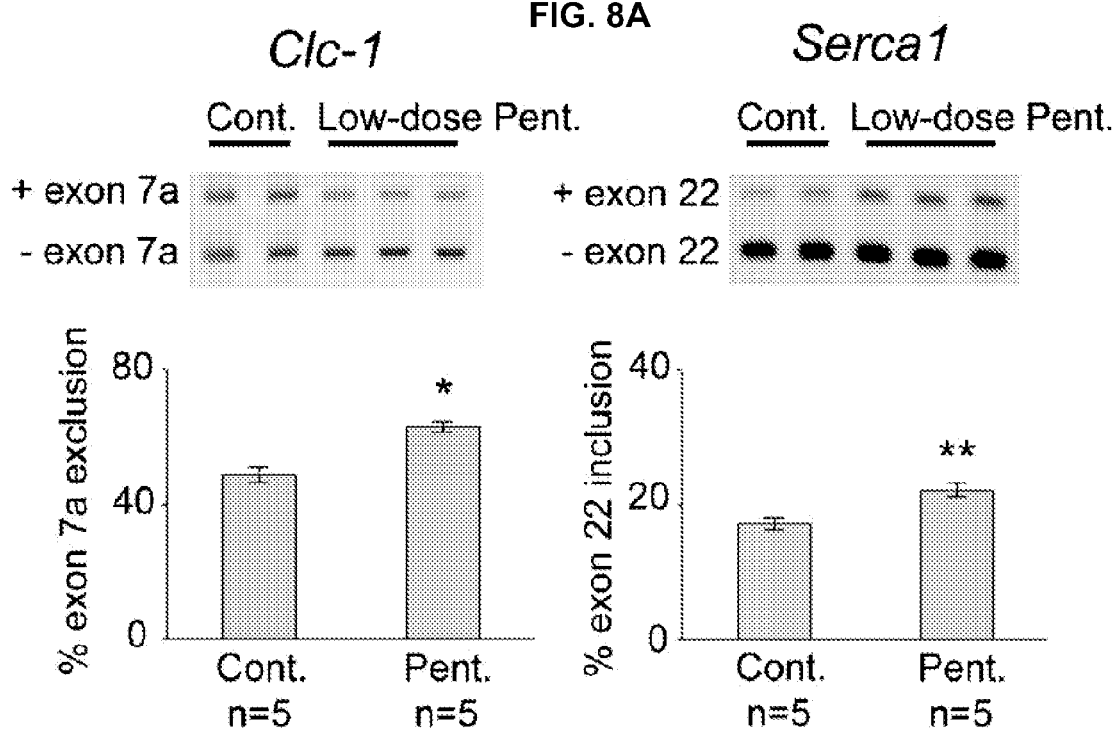
FIG. 8A shows photographs of gels showing splicing of exon 7a of chloride channel 1 (Clc-1) and exon 22 of sarcoplasmic reticulum/endoplasmic reticulum $Ca^{2+}$ ATPase (Serca1) in mice treated with low-dose pentamidine treatment (25 mg/kg twice daily for 5 days) or control mice (top) and histograms showing the mean percentages of Clc-1 exon 7a exclusion and Serca1 exon 22 inclusion (bottom). *$p<0.001$, **$p<0.01$. Error bar indicates mean±SEM.
Figure 8B:
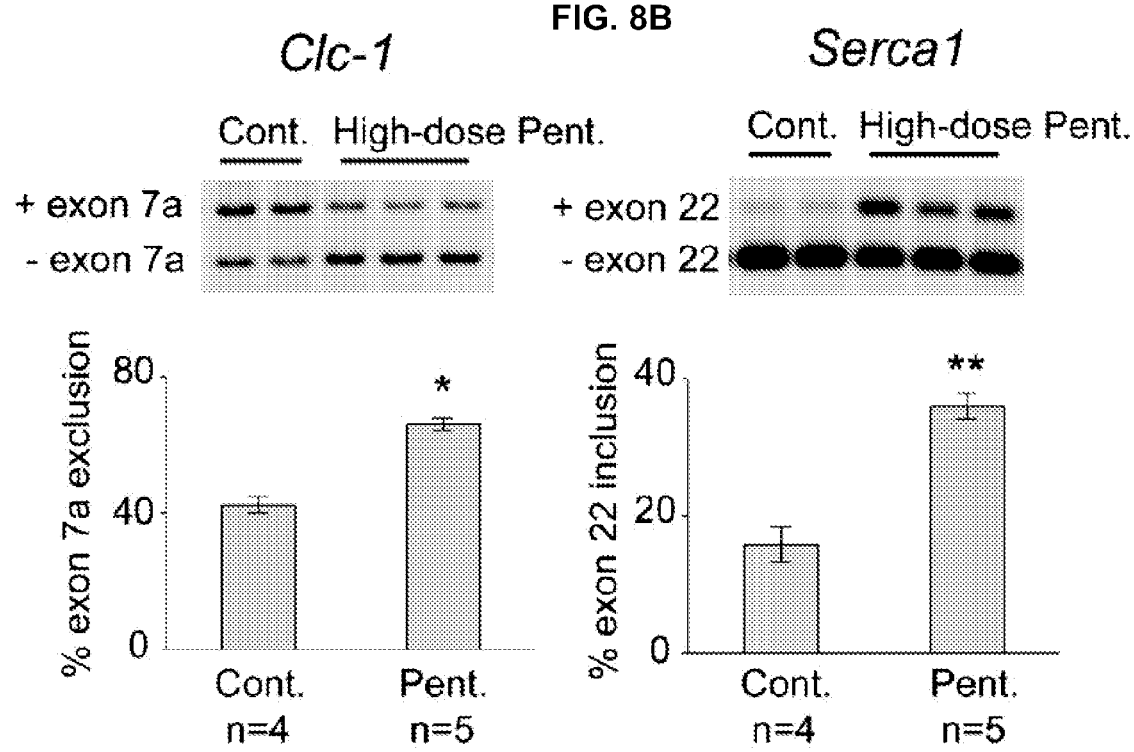
FIG. 8B shows photographs of gels showing splicing of exon 7a of Clc-1 and Serca1 in mice treated with high-dose pentamidine treatment (40 mg/kg once daily for 7 days) or control mice (top) and histograms showing the mean percentages of Clc-1 exon 7a exclusion and Serca1 exon 22 inclusion (bottom). *$p<0.001$, **$p<0.01$. Error bar indicates mean±SEM.

This example describes the effect of pentamidine in a mouse model of DM, which expresses an expanded 250 CUG repeat.
Methods
Mouse handling and experimental procedures were conducted in accordance with the Association for Assessment and Accreditation of Laboratory Animal Care. $HSA^{LR}$ transgenic mice in line 20b expressing human skeletal actin mRNA with ~250 CUG repeats in the 3' UTR were used (Mankodi et al., Science 289:1769-1772, 2000). Age- and gender-matched $HSA^{LR}$ mice were injected intraperitoneally with pentamidine or saline (control). For a low-dose regimen, 25 mg/kg of pentamidine was administrated twice daily for 5 days. For a higher-dose regimen, 40 mg/kg of pentamidine was injected once daily for 7 days. Mice were sacrificed one day after the last injection, and vastus muscle was obtained for splicing analysis. RNA extraction and cDNA preparation were performed as described in Example 3. PCR amplification was carried out for 22-24 cycles with the following primer pairs: Clc-1 forward, TGAAGGAATACCTCACACT-CAAGG (SEQ ID NO: 7), and reverse, CACGGAACA-CAAAGGCACTG (SEQ ID NO: 8); Serca1 forward, GCT-CATGGTCCTCAAGATCTCAC (SEQ ID NO: 9), and reverse, GGGTCAGTGCCTCAGCTTTG (SEQ ID NO: 10). The PCR products were analyzed on agarose gels and scanned with a laser fluorimager (Typhoon, GE Healthcare, Piscataway, N.J.). Differences between the two groups were evaluated by Student's t-test.
Results
The ability of pentamidine to rescue mis-splicing in a mouse model ($HSA^{LR}$) where CUG repeats are expressed was tested. Pentamidine was administered by intraperitoneal injection in two dosage regimens, and mis-splicing of the Clc-1 and Serca1 pre-mRNAs was measured. MBNL is known to repress inclusion of exon 7a in the Clc-1 mRNA and enhance inclusion of exon 22 in the serca1 mRNA (Kimura et al., Hum. Mol. Genet. 14:2189-2200, 2005). The lower dosage regimen had a modest, but significant rescue of mis-splicing of both transcripts when compared to control mice injected with only saline (FIG. 8A). Mice normally have a Clc-1 exon 7a exclusion of 94±1%, while the $HSA^{LR}$ line has a level of exon 7a exclusion of 46±6%. Pentamidine treatment at the lower dosage partially rescued exon 7a exclusion to 63±3% (FIG. 8A), while the higher dosage regimen rescued exon 7a exclusion to 66±4% exclusion (FIG. 8B). Inclusion of the Serca1 exon 22 is normally seen to be 99.7±0.1%, while $HSA^{LR}$ mice have levels of exon 22 inclusion of 17±4%. Lower dosage pentamidine treatment minimally rescued exon 22 inclusion to 22±2% (FIG. 8A), while the higher dosage treatment more significantly rescued it to 40±4% (FIG. 8B). Further increases to the dosage regimens had substantial toxicity in the mice. However, the partial rescue that was observed was statistically significant.

Example 6

Testing of Pentamidine and Derivatives in a Drosophila Model of DM

This example describes testing of pentamidine in a Drosophila model of DM, which overexpresses 480 interrupted non-coding CUG repeats.

A Drosophila DM model, such as a transgenic Drosophila expressing a non-coding mRNA containing 480 interrupted CUG repeats (de Haro et al., Hum. Mol. Genet. 15:2138-2145, 2006), is used to evaluate pentamidine in an in vivo model of DM. Pentamidine or other test compound is added to the fly food at doses ranging from 5 µM to 125 µM beginning at the larval stage and continuing throughout life. The effectiveness of test compounds to reverse the defects caused by the CUG repeats in the Drosophila DM model is assessed by comparing treated and untreated flies. To assess muscle degeneration, muscle cells from 15-day and 25-day old flies are examined. Muscle degeneration is measured by determining the size of vacuoles compared to the cell size. Disorganization in the Drosophila eye, which results from expression of expanded CUG repeats, is monitored by scanning electron microscopy.

Administration of pentamidine, pentamidine derivatives, or other test compound is expected to decrease muscle degeneration, for example by decreasing the size of muscle cell vacuoles compared to the cell size, when compared with untreated control flies. Similarly, treatment is expected to decrease disorganization in the structure of the eye, when compared with untreated control flies.

Example 7

Structure Determination of Pentamidine and Related Compounds in Complex with CUG Repeats This example describes the crystallization of pentamidine and related compounds with CUG repeats to facilitate rational design of CUG-specific compounds.

Crystals of an 18 oligonucleotide RNA containing six CUG repeats ($CUG_6$) with pentamidine or other small molecules are generated. The protocol of Mooers et al. (Proc. Natl. Acad. Sci. USA 102:16626-16631, 2005) is used for purification and crystallization.

One approach is co-crystallization of the small molecule with the RNA. This entails mixing the small molecule with the RNA before the crystallization. A range of small molecule concentrations is used, from an equal molar concentration of small molecule and RNA to 50-fold molar excess of small molecule to RNA. Concentrations of the salt, precipitant and other conditions of the crystallization trials are varied in order to obtain co-crystals.

Crystals of the $CUG_6$ repeat may also be obtained following the protocol of Mooers et al. and then soaking in the small molecules into the $CUG_6$ crystals. Concentrations of small molecules (such as pentamidine) from 150 µM to 2 mM are used. Soaking times range from 30 minutes to 2 days.

In addition, in both approaches, the length of the CUG repeat may be varied, for example utilizing RNAs containing three to ten CUG repeats.

Crystal structures are solved using either molecular replacement with the CUG$_6$ structure as a model or using RNA containing modifications such as bromo-uridine and iodo-uridine, which can be used to determine the structure using multiple isomorphous replacement or multi-wavelength anomalous dispersion methods.

The above methods are also applied to determining the crystal structure of additional RNA nucleotide repeat expansions which are associated with disease. For example, the structure of a CCUG repeat (such as an RNA containing three to ten CCUG repeats) may be solved in the presence and absence of pentamidine or pentamidine derivatives. Likewise, the structure of a CGG repeat (such as an RNA containing three to ten CGG repeats) may be solved in the presence and absence of pentamidine or pentamidine derivatives.

The resulting structures are used to design additional test compounds for use in the methods described above for treating diseases caused by toxic RNA.

Example 8

Synthesis of Diamidine Derivatives

This example describes methods of synthesis of exemplary diamidine derivatives.

One example of a diamidine derivative is a diamidine wherein a benzene ring is included in the carbon linker. The derivative is synthesized by nucleophilic substitution of the bromine atoms in α,α'-dibromo-m-xylene by hydroxybenzonitrile in aqueous sodium hydroxide to yield a bisbenzonitrile intermediate. This can be transformed by reaction with hydrochloric acid in ethanol and dichloromethane to the corresponding imidate. The imidate can be converted by to the amidine by refluxing with ammonia saturated ethanol. See, e.g., Vanden Eynde et al., *Med. Chem. Res.* 14:143-157, 2005; Chauhan et al., *Ind. J. Chem.* 27B:38-42, 1988.

An example of the synthesis of the corresponding pentamidine derivative is as follows:

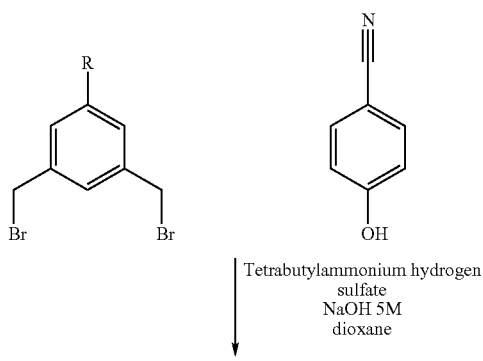

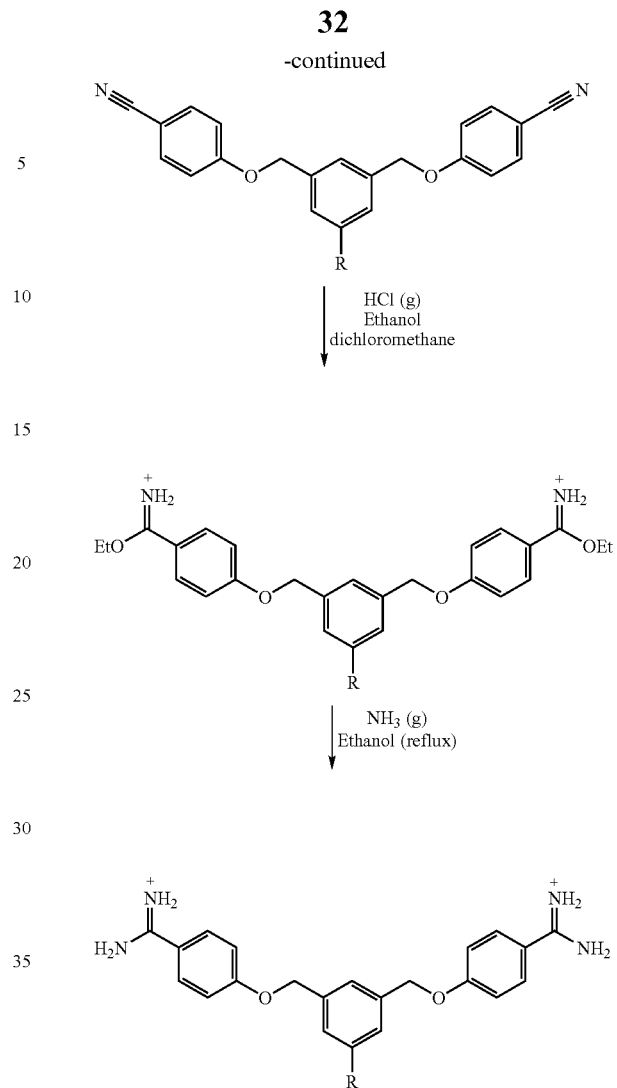

Another example of a diamidine derivative is a diamidine oligomer having a meta linkage. The meta-linked oligomer is synthesized by pouring dibromopentane into a stirred solution of 4-cyanophenol in ethanol containing sodium ethoxide. The resulting mixture is separated by chromatography and compounds of the desired length are reacted with ethanol and hydrogen chloride in toluene to provide the imidate intermediate which is isolated but not purified. The polyimidate is then reacted with ammonia saturated ethanol to yield the desired polyamidine.

An example of the synthesis of the meta-linked pentamidine oligomer is as follows:

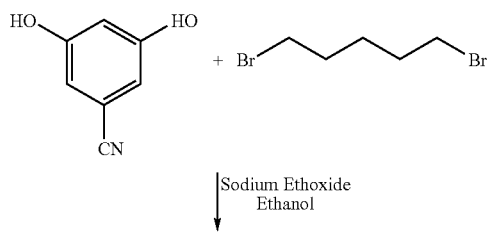

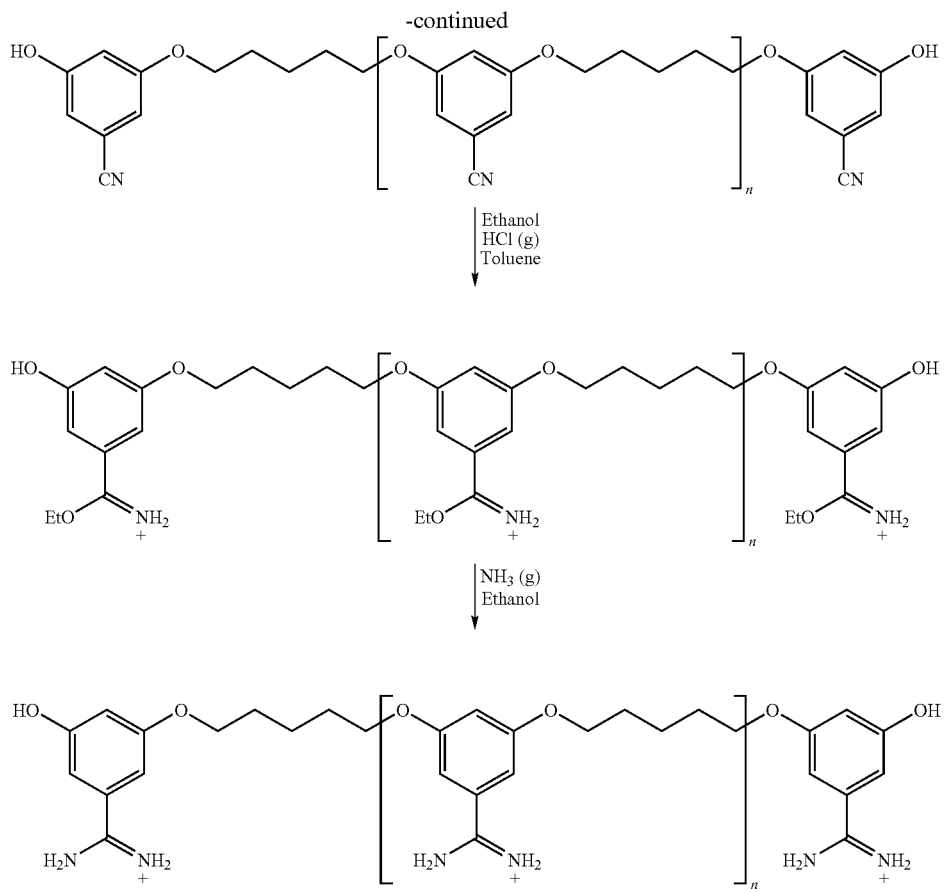

Another example of a diamidine derivative is a diamidine trimer having a meta-para linkage. The meta-para oligomer is synthesized by nucleophilic substitution of one bromine atom in 1,5-dibromopentane (used in large excess) by both oxygen atoms of a 3,4-dihydroxybenzonitrile sodium ethoxide containing ethanol solvent giving the 3,4-Bis-(5-bromo-pentyloxy)-benzonitrile. This benzonitrile is dissolved in ethanol and added to a solution containing 2 equivalents of 4-hydroxybenzonitrile and sodium ethoxide in ethanol providing the 3,4-Bis-[5-(4-cyano-phenoxy)-pentyloxy]-benzonitrile. Reaction of 3,4-Bis-[5-(4-cyano-phenoxy)-pentyloxy]-benzonitrile with ethanol and hydrogen chloride in toluene converts all cyano groups in the starting materials to the imidate which is isolated but not purified. The tris imidate compound is reacted with ammonia saturated ethanol to yield the desired tris amidine.

An example of the synthesis of the meta-para linked pentamidine trimer is as follows:

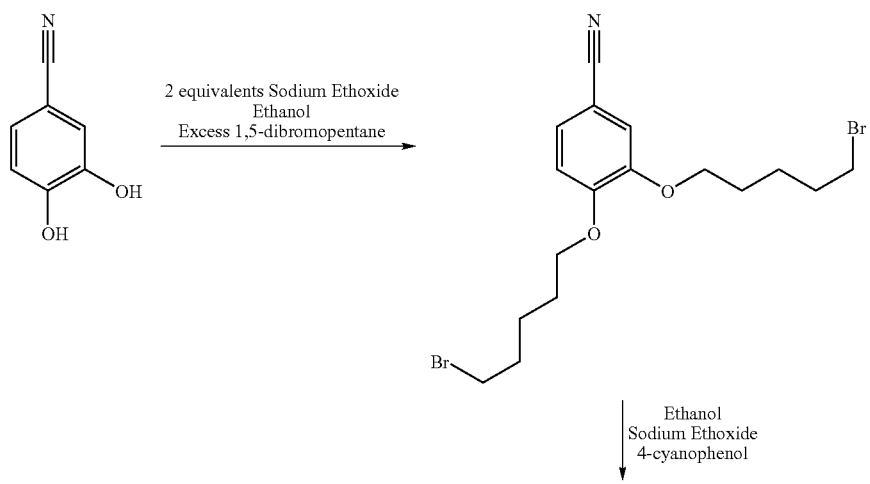

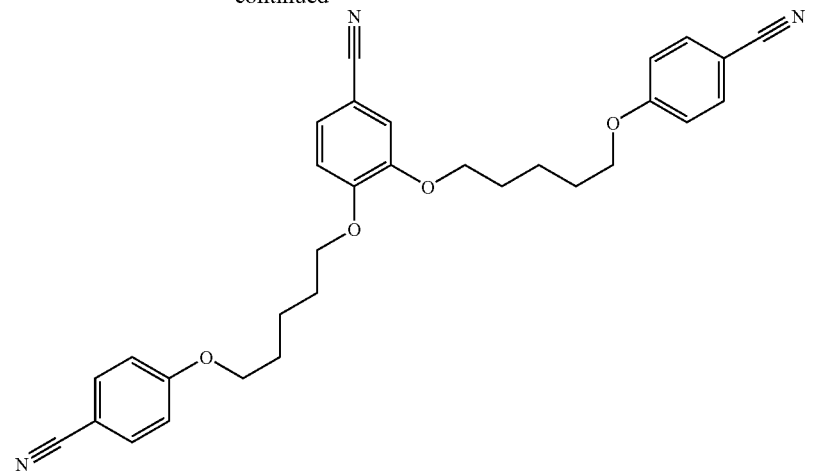
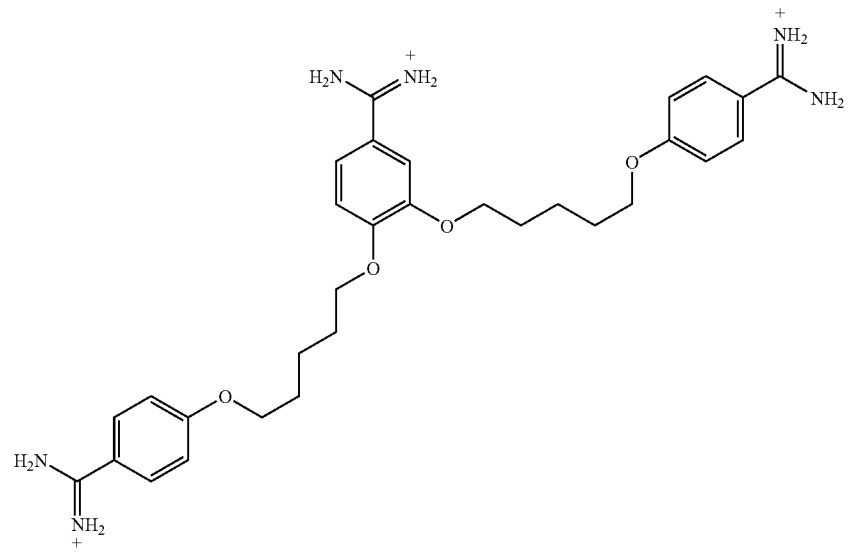
An example of the synthesis of the unsaturated para-linked hexamidine is as follows:
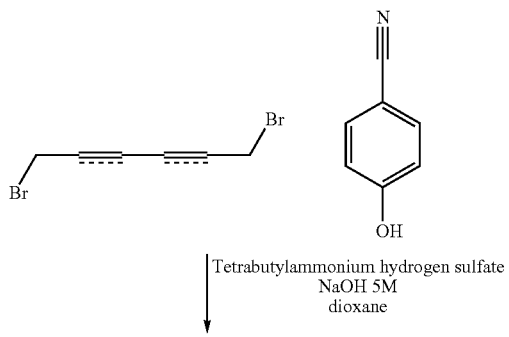
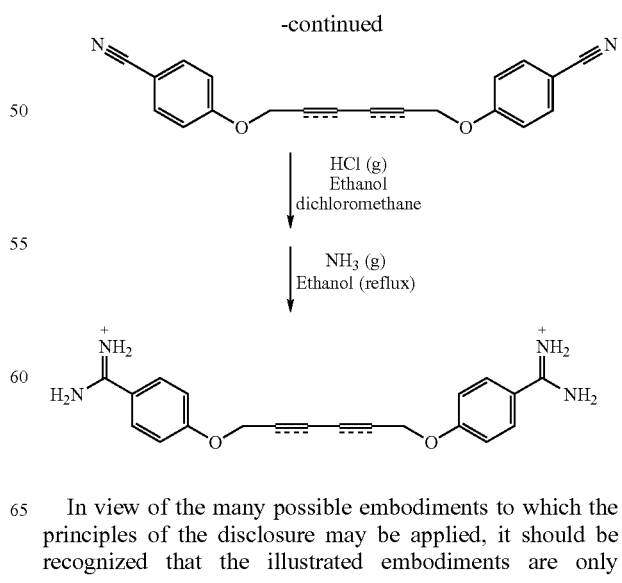
In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of treating myotonic dystrophy in a subject, comprising administering to the subject a compound, diamidine having the structure

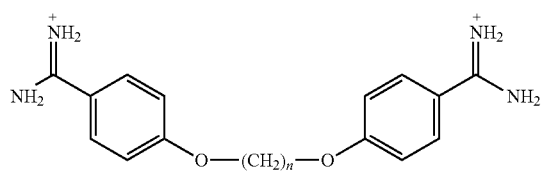

wherein n=2–7, that binds a nucleotide repeat expansion in a ribonucleic acid molecule, thereby treating myotonic dystrophy.

2. The method of claim 1, wherein the nucleotide repeat expansion comprises a trinucleotide repeat expansion.

3. The method of claim 2, wherein the trinucleotide repeat expansion comprises a CUG repeat.

4. The method of claim 1, wherein the nucleotide repeat expansion comprises a trinucleotide repeat expansion in the pre-mRNA or mRNA of the dystrophia myotonica-protein kinase gene.

5. The method of claim 1, wherein the nucleotide repeat expansion comprises a tetranucleotide repeat expansion.

6. The method of claim 5, wherein the tetranucleotide repeat expansion comprises a CCUG repeat.

7. The method of claim 1, wherein the nucleotide repeat expansion comprises a tetranucleotide repeat expansion in a zinc finger 9 ribonucleic acid.

8. The method of claim 1, wherein the diamidine comprises pentamidine or heptamidine.

9. The method of claim 1, wherein the compound diamidine having the structure

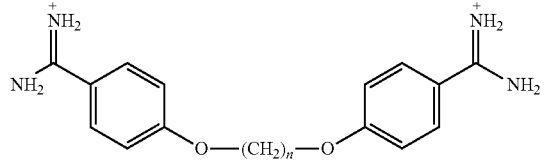

wherein n=2–7, that binds the nucleotide repeat expansion disrupts the binding of muscleblind-like proteins to CUG repeats of dystrophia myotonica-protein kinase.

10. The method of claim 1, wherein the compound diamidine having the structure

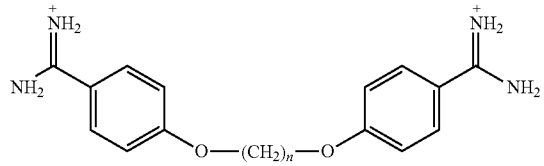

wherein n=2–7, that binds the nucleotide repeat expansion disrupts binding of muscleblind-like proteins to CCUG repeats within intron 1 of zinc finger 9 pre-mRNA.

11. A method of treating myotonic dystrophy caused by toxic RNA in a subject, comprising administering to the subject a compound, diamidine having the structure

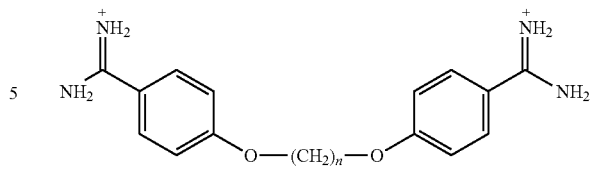

wherein n=2–7, that binds a nucleotide repeat expansion in a ribonucleic acid molecule, thereby treating the disease caused by toxic RNA.

12. A method of treating myotonic dystrophy caused by toxic RNA in a subject, comprising administering to the subject a compound, diamidine having the structure

wherein n=2–7, that displaces muscleblind-like (MBNL) protein from a nucleotide repeat expansion in a ribonucleic acid molecule, thereby treating the disease caused by toxic RNA.

13. The method of claim 11, wherein the diamidine comprises pentamidine or heptamidine.

* * * * *

UNITED STATES PATENT AND TRADEMARK OFFICE
CERTIFICATE OF CORRECTION

PATENT NO.        : 8,436,049 B2            Page 1 of 1
APPLICATION NO.   : 12/918696
DATED             : May 7, 2013
INVENTOR(S)       : Berglund et al.

It is certified that error appears in the above-identified patent and that said Letters Patent is hereby corrected as shown below:

In the Specification:

Column 19, line 25, "2005) Immortalized" should read --2005). Immortalized--.

Column 26, lines 64-65, "GTACAAGCTTGAATGCTGCTCCTGTCCAAGACAG (SEQ ID NO: 3)" should read --<u>GTACAAGCTT</u>GAATGCTGCTCCTGTCCAAGACAG (SEQ ID NO: 3)--.

Column 26, lines 66-67, "GCCCTCGAGCGTGGGCACGCTGGTC (SEQ ID NO: 4)" should read --<u>GCCCTCGAG</u>CGTGGGCACGCTGGTC (SEQ ID NO: 4)--.

Signed and Sealed this
Eighth Day of September, 2015

Michelle K. Lee
*Director of the United States Patent and Trademark Office*